(12) United States Patent
Chung et al.

(10) Patent No.: US 9,034,327 B2
(45) Date of Patent: May 19, 2015

(54) G PROTEIN COUPLED RECEPTOR PROTEIN AND USE THEREOF

(75) Inventors: Kyung Sook Chung, Daejeon (KR); Mi Sun Won, Daejeon (KR); Ji Won Ahn, Nonsan-si (KR); Jeong Hae Choi, Busan (KR); Hyang Sook Yoo, Daejeon (KR); Young Il Yeom, Daejeon (KR); Eun Young Song, Seoul (KR); Hee Gu Lee, Daejeon (KR); Jae Hun Cheong, Busan (KR); Chang Mo Kang, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/322,304

(22) PCT Filed: Sep. 7, 2009

(86) PCT No.: PCT/KR2009/005062
§ 371 (c)(1),
(2), (4) Date: Dec. 13, 2011

(87) PCT Pub. No.: WO2010/137770
PCT Pub. Date: Dec. 2, 2010

(65) Prior Publication Data
US 2012/0141488 A1 Jun. 7, 2012

(30) Foreign Application Priority Data

May 25, 2009 (KR) .................. 10-2009-0045519

(51) Int. Cl.
G01N 33/53 (2006.01)
C07K 14/705 (2006.01)
G01N 33/50 (2006.01)

(52) U.S. Cl.
CPC .......... *C07K 14/705* (2013.01); *G01N 33/5041* (2013.01)

(58) Field of Classification Search
None
See application file for complete search history.

(56) References Cited

U.S. PATENT DOCUMENTS

| 7,368,531 B2 * | 5/2008 | Rosen et al. .................. 530/350 |
| 7,713,699 B2 | 5/2010 | Feder et al. |
| 2007/0149449 A1 | 6/2007 | Morris et al. |

FOREIGN PATENT DOCUMENTS

| EP | 1382613 | 1/2004 |
| WO | WO 01/36432 A2 | 5/2001 |
| WO | WO 03068803 | 8/2003 |

OTHER PUBLICATIONS

Extended Search Report from EP 09845277.1 dated Aug. 10, 2012.
GenBank Accession No. CAI22229.1, Jan. 9, 2009.
NCBI Reference Sequence: NP 060235.1, Sep. 23, 2005.
Ponting, C. et al.: "Novel Protein Domains and Repeats in *Drosophila melanogaster*: Insights into Structure, Function, and Evolution"; Genome Res. 2001, vol. 11; pp. 1996-2008.
Van Dijck, P.: "Nutrient sensing G protein-coupled receptors: interesting targets for antifungals?"; Medical Mycoloty, 2009; pp. 1-10.

* cited by examiner

*Primary Examiner* — Michael Pak
(74) *Attorney, Agent, or Firm* — Lathrop & Gage LLP; Andrew T. Wilkins, Esq; Brian C. Trinque, Esq

(57) ABSTRACT

Disclosed are novel GPCR (G Protein Coupled Receptor) proteins and genes encoding the same. Also provided is the use of the proteins and the genes. Particularly, contemplated are a novel GPCR (G Protein Coupled Receptor) polypeptide, a polynucleotide coding for the same, a recombinant vector carrying the polynucleotide or a fragment thereof, host cells transformed with the vector, a transgenic animal infected with the vector. Also, a composition for detecting a cancer marker, comprising an agent capable of measuring the expression level of mRNA or protein of the GPCR polynucleotide, a kit for the diagnosis of cancer, comprising the composition, and a method for detecting the GPCR polypeptide and a gene encoding the polypeptide are provided. Further, a composition for the treatment and prevention of cancer, comprising an oligonucleotide inhibiting the expression of a gene encoding the GPCR polypeptide or an antibody against the GPCR protein, and a method for screening a modulator of the GPCR protein or a cancer therapeutic agent are provided.

4 Claims, 10 Drawing Sheets

Fig. 1
A
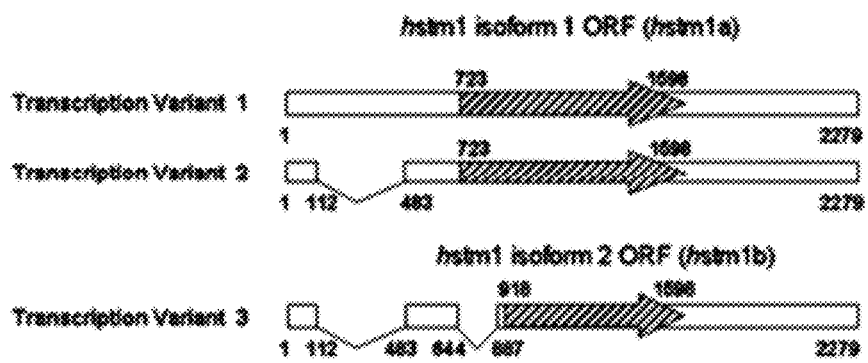
B
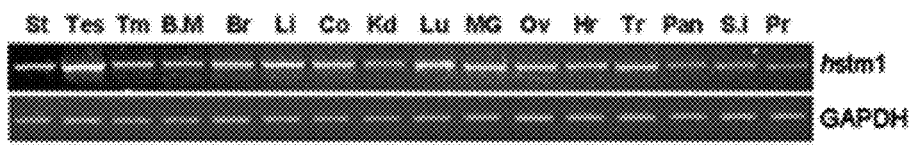
C
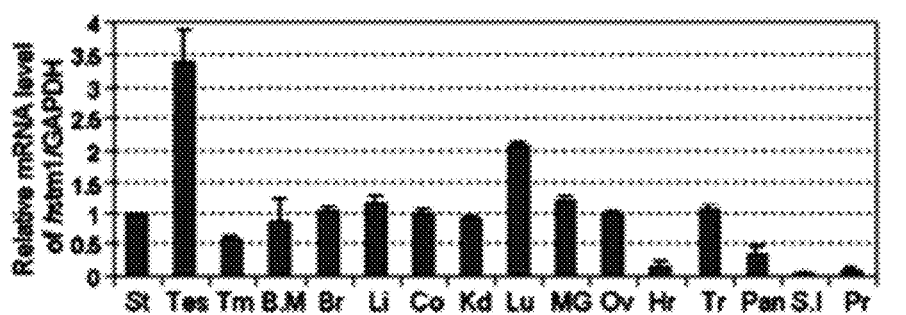
St: Stomach, Tes:Testis, Tm:Thymus, BM:Bone marrow, Br:Brain Li:Liver
Co:Colon, Kd:Kidney, Lu:Lung, MG:Mammary gland, Ov:Ovary, Hr:Heart,
Tr:Thyroid, Pan:Pancreas, SI:Small intestine, Pr:Prostate

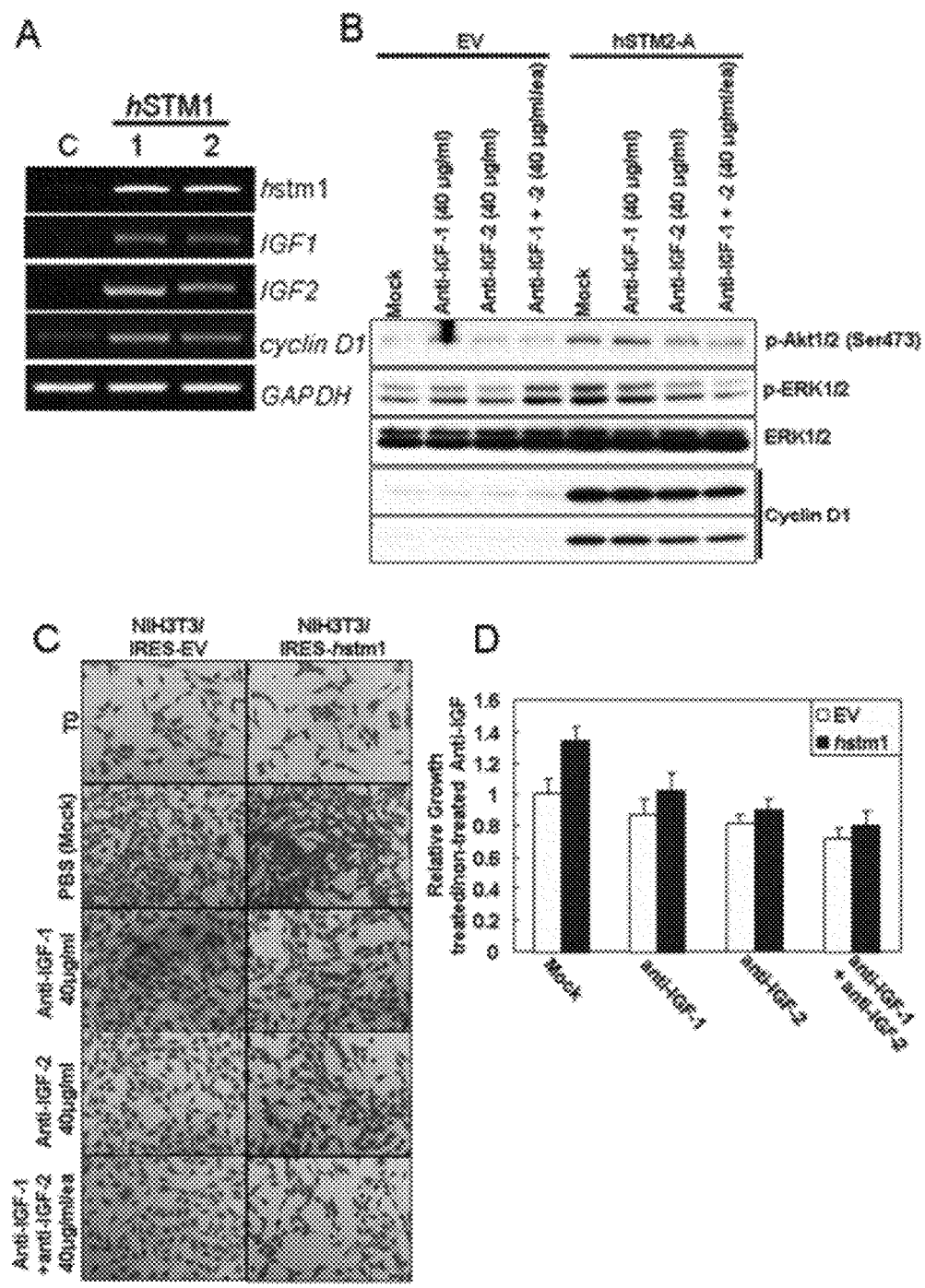

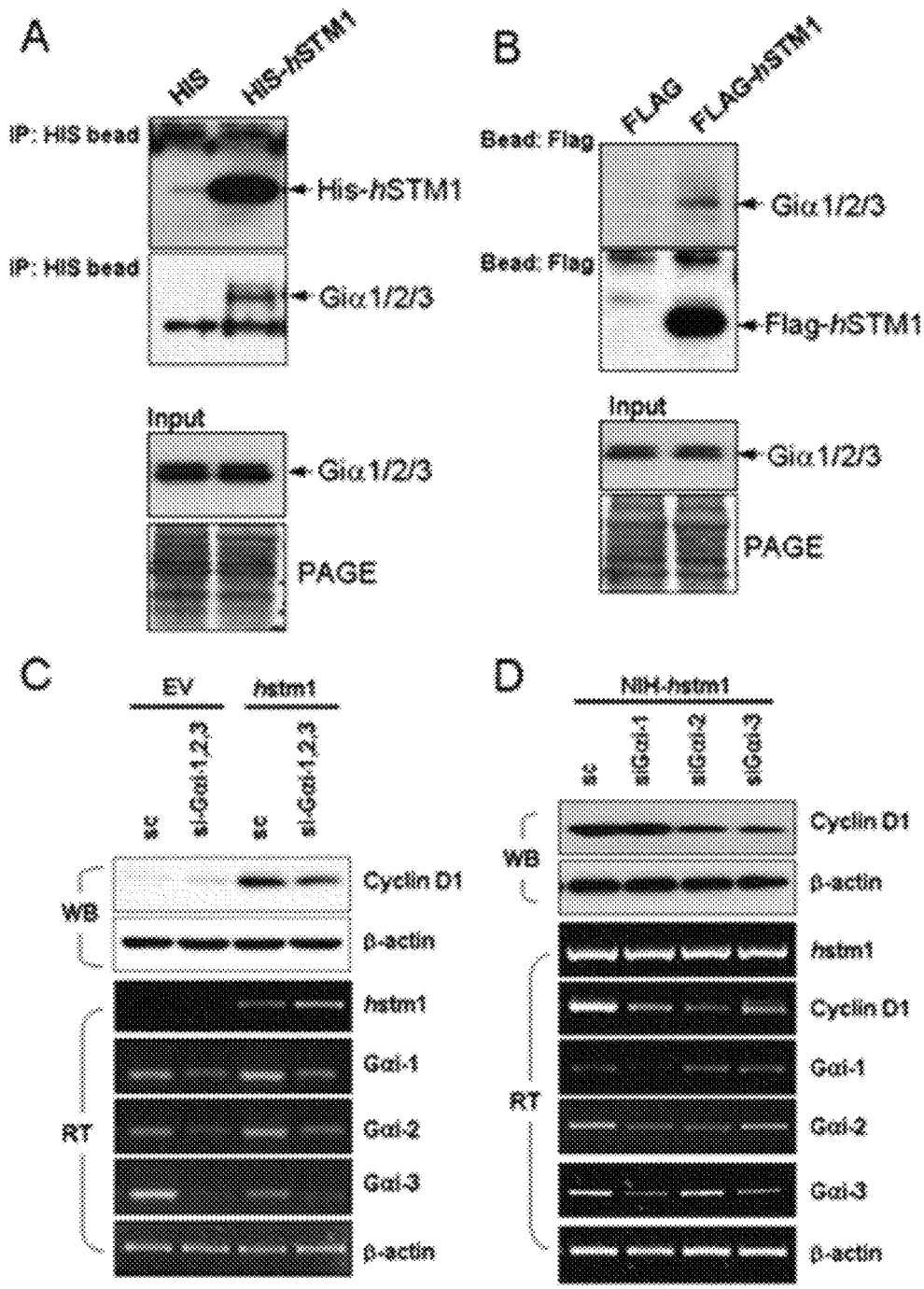

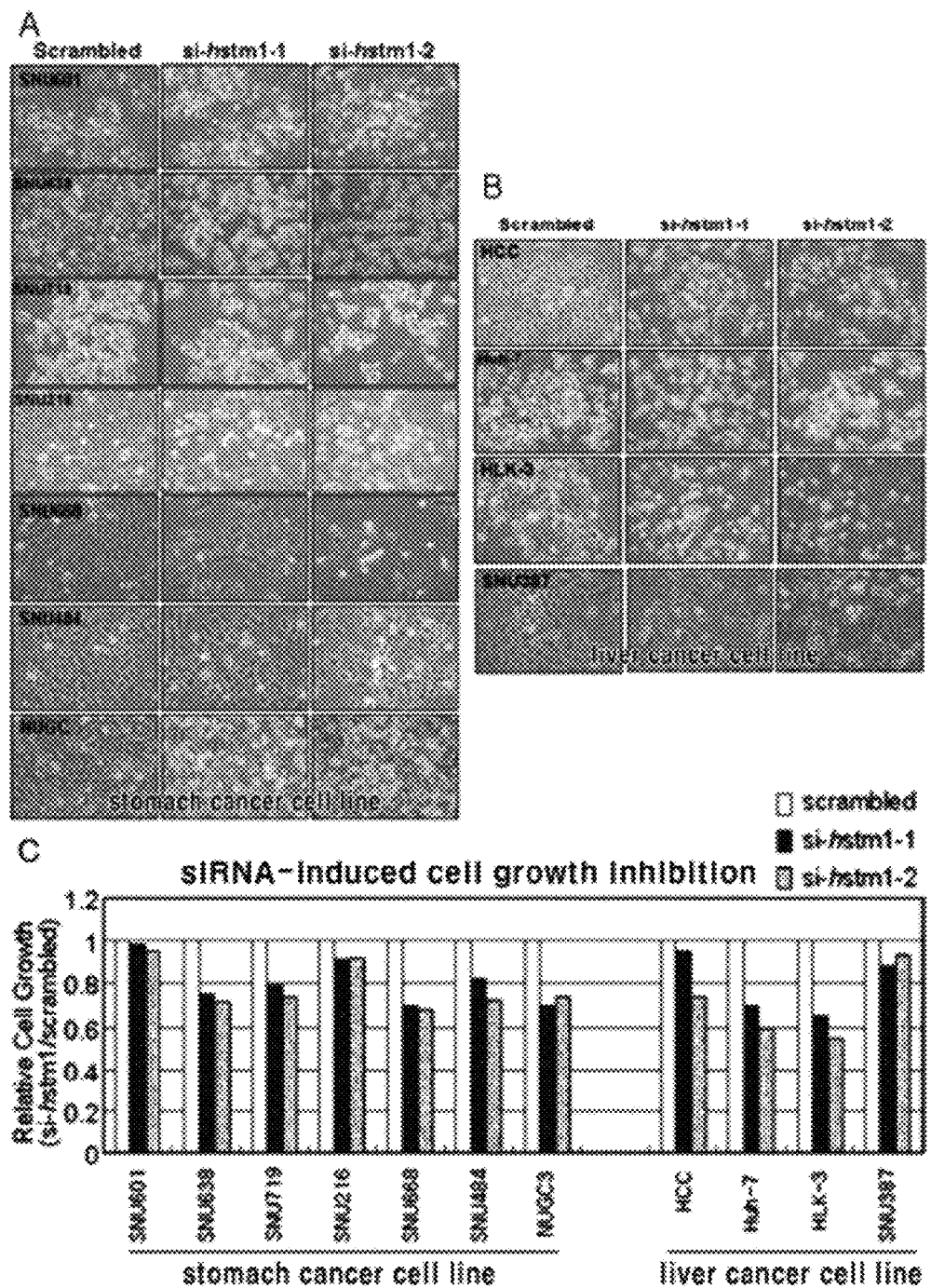

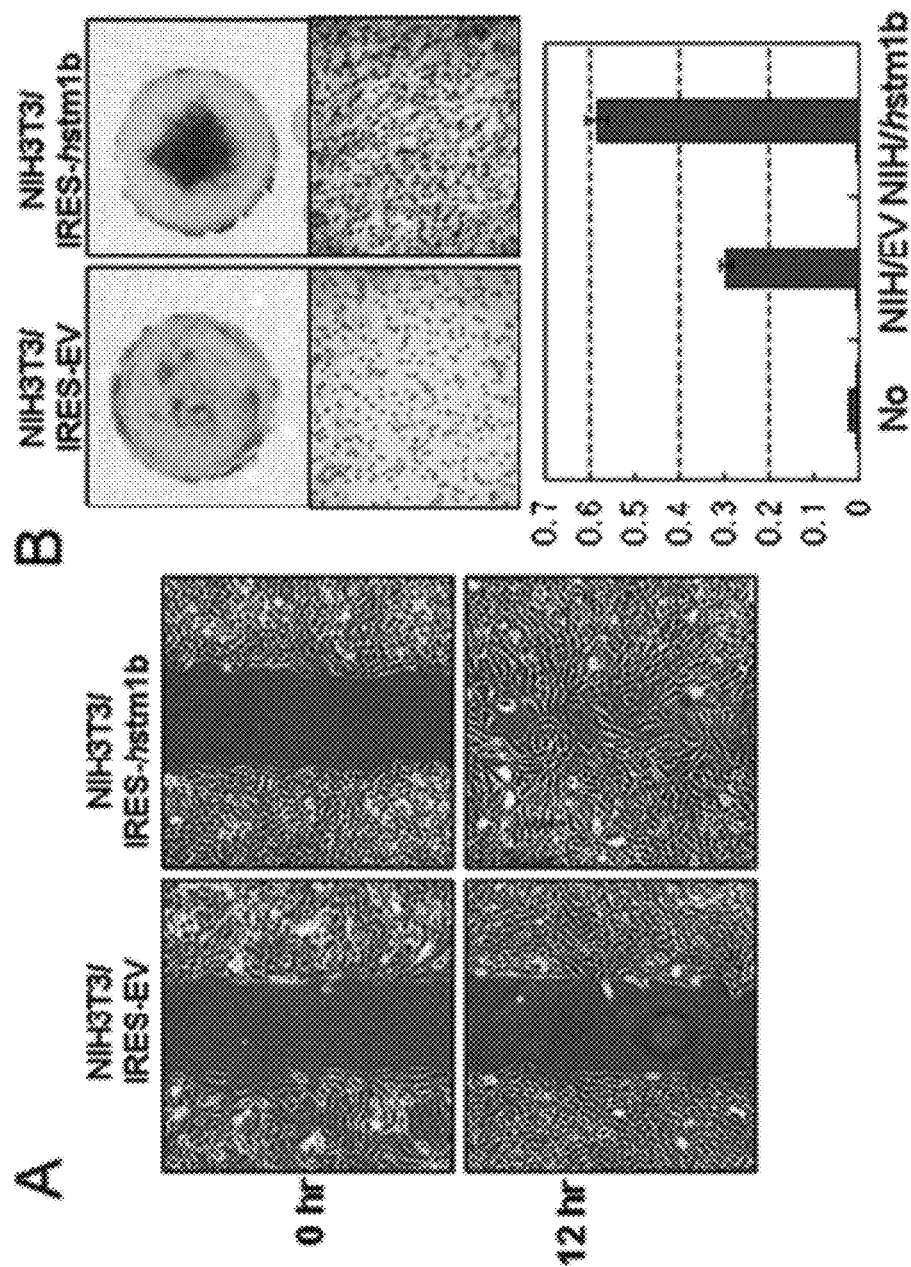

US 9,034,327 B2

G PROTEIN COUPLED RECEPTOR PROTEIN AND USE THEREOF

RELATED APPLICATIONS

This application is a 35 U.S.C. §371 filing of International Patent Application No: PCT/KR2009/005062 which was filed on Sep. 7, 2009, which claims priority to Korean Patent Application No: 10-2009-0045519, which was filed on May 25, 2009. The entire contents of the aforementioned applications are hereby incorporated herein by reference.

TECHNICAL FIELD

The present invention is a novel G protein-coupled receptor (GPCR) protein, a gene encoding the same, and novel uses thereof. More particularly, the present invention relates to a novel GPCR (G Protein Coupled Receptor) polypeptide, a polynucleotide encoding the same, a recombinant vector carrying the polynucleotide or a fragment thereof, host cells transformed with the vector, and a transgenic animal transformed with the vector. Also, the present invention relates to a composition for detecting a cancer marker, comprising an agent capable of measuring the expression level of mRNA or protein of the GPCR polynucleotide of the present invention, a kit for the diagnosis of cancer, comprising the composition, and a method for detecting the GPCR polypeptide of the present invention and a gene encoding the polypeptide. In addition, the present invention relates to a composition for the treatment and prevention of cancer, comprising an oligonucleotide inhibiting the expression of a gene encoding the GPCR polypeptide of the present invention or an antibody against the GPCR protein of the present invention, and a method for screening a modulator of the GPCR protein of the present invention or a cancer therapeutic agent.

BACKGROUND ART

Human cells have a variety of receptors on their surfaces. Inter alia, G-protein coupled receptors (hereinafter referred to as "GPCR" or "GPCRs") comprise one of the largest protein families of transmembrane receptors. The human genome retains approximately 30,000 human genes, as many as 1000 of which are known to encode GPCRs. On the basis of recent studies conducted on vertebrate genomes, GPCRs have been grouped into five classes. The first class comprises a rhodopsin receptor family to which 670 receptor proteins belong. This rhodopsin receptor family can react with various ligands including amines (alpha group), peptides (beta group), lipid-like substances (gamma group), nucleotides, and glycoproteins (delta group), and comprises a lot of drug target receptors. The second class addresses the secretin receptor family and has binding domains for peptide hormones. Receptors in this family are associated with homeostasis and have been arising as important targets for drug development. The third class is assigned the adhesion receptor family, characterized by a GPCR proteolytic site (GPS). The development of drugs targeting GPCR members of this family has not yet taken place because they exhibit various N-terminal moieties and little is known about their ligands. Within the fourth class is the glutamate receptor family in which 22 GPCR members have so far been identified. Relatively little is known about the specificity of each protein. The last class is the Frizzled/Taste2 family that encompasses 10 Frizzled receptors for which Wnt glycoproteins serve as ligands, 5 SMO (smoothened) receptors which need no ligands, and 25 Taste2 receptors which are required for sensing various tastes. Receptors including GPCRs are also classified on the basis of the identification of endogenous ligands. Receptors bind with known endogenous compounds or are classified as orphan receptors whose endogenous ligands have not yet been identified.

GPCRs are found in a broad range of types of tissues and cells and are associated with many different physiological mechanisms. They are activated by a wide range of ligands, for example, hormones such as thyroid-stimulating hormone (TSH), adrenocorticotropic hormone, glucagon and vasopressin, amines such as 5-HT, acetylcholine (muscarinic AchR), and histamines, lipids such as LPA and S1P, and signal transmitters such as amino acids, $Ca^{2+}$, nucleic acids, peptides and light. The wide distribution and diversity of roles that GPCRs play is evidence to the important roles that they play in various pathological diseases. Indeed, GPCRs are known to be involved in various diseases including bronchoconstriction, hypertension, diabetes, inflammation, hormone disorders, cell death, cancer, neurotransmission and behavioral disorders. Currently, GPCRs are therefore an area that is important to the development of pharmaceutical products. Approximately 360 GPCRs are now considered available for drug development. Of these, 46 have already been used for drug development while the remaining about 320 genes can be exploited for drug development. There are approximately an estimated 150 Orphan GPCRs (oGPCRs). In the field of new drug development, cell membrane receptors act as selective sites for drug action and are responsible for 50% of all drug targets (Nature Reviews Drug Discovery, 2004. 2008) and GPCR activity modulating drugs, inter alia, account for 30% of the most frequently used top 100 drugs (40 billion dollars, 9% of the total drug market). Therefore, GPCR is one of the most significant targets for the development of new drugs (Nature Reviews Drug Discovery, 2004, 2008).

GPCRs have common structural features. All of these receptors have seven hydrophobic membrane-spanning domains, each 20~30 amino acids long, which are connected by hydrophilic amino acid sequences of various lengths. The receptors have an extracellular N-terminus while the C-terminus is located in the cytoplasm. GTP-binding proteins (G proteins) act as mediators transmitting to intracellular effectors the signals that are generated by binding hormones or other chemical ligands that stimulate GPCR. After a ligand has become bound to GPCR, the intracellular domains of the receptor undergo a conformational change which allows the receptor to interact with G protein, which in turn activates intracellular signal transmitters such as adenylate cyclase, phospholipase C or ion channel. This system generates a signaling cascade in which many secondary transmitters act in response to the binding of one ligand to GPCR. This mechanism is used by cells to detect extracellular environmental changes and to properly react in response to the changes. On the whole, receptors are activated by endogenous ligands with the concomitant generation of a conformational change, which allows association between the receptors and the G-proteins. Recent studies on the interaction between proteins have revealed that GPCR is associated with various proteins such as GRK or SH2 domain (src homology 2 domain)-containing proteins, and adaptor Grb2 as well as G protein to participate in signaling transduction.

Under normal conditions, signaling transduction brings about the final result which is cell activation or suppression. In a physiological environment, GPCRs exist in equilibrium between their inactive and active states in the cell membrane. Inactive receptors cannot exert a biological response in conjunction with cellular signal transduction pathways. The receptors can exhibit biological responses via a signal transduction pathway (through G-proteins) only when they have structurally changed to their active form. The receptor may be stabilized into an active form by compounds such as endogenous ligands or drugs. Therefore, functional studies, such as the cloning of such gene families, and the identification of new ligands thereof, have the same meaning as the development of new drug candidates, that is, siRNA, antibodies, polypeptides, effectors, inhibitors, agonists, antagonists, etc.

Development, differentiation, homeostasis, responses to stimuli, control of the cell cycle, as well as the aging and apoptosis of living organisms are mostly a result of the selective expression of specific genes within cells. This is true for cellular mechanisms associated with diseases. Particularly, pathological phenomena, such as oncogenesis, are induced by gene mutations that in the end lead to changes in gene expression.

According to various studies into oncogenesis, the generation of tumors is the result of the accumulation of various genetic changes such as the loss of chromosomal heterozygosity, the activation of oncogenes, the inactivation of tumor suppressor genes including p53 gene, etc. (Bishop, J. M., Cell, 64:249-270 (1991)). Further, the activation of oncogenes by oncogene amplification was reported to account for 10-30% of cancer cases. Thus, the activation of oncogenes is significant to the pathological study of various cancers. There is an imminent need for identifying oncogenes and developing a method of controlling the oncogenes.

DISCLOSURE

Technical Problem

Leading to the present invention, intensive and thorough research into the identification of oncogenes, resulted in cloning a putative orphan GPCR gene and in the finding that the overexpression of the gene induces oncogenesis.

Technical Solution

It is an object of the present invention to provide a GPCR (G Protein Coupled Receptor) polypeptide having the amino acid sequence of SEQ ID NO: 1 or 2.

It is another object of the present invention to provide a polynucleotide encoding the polypeptide.

It is a further object of the present invention to provide a recombinant vector carrying the polynucleotide or a fragment thereof.

It is still a further object of the present invention to provide a host cell transformed with the vector.

It is still another object of the present invention to provide a transgenic animal delivered by a surrogate mother in the womb of which a host cell transformed with the vector is implanted.

It is yet a further object of the present invention to provide a composition for detecting a cancer marker, comprising an agent capable of measuring the expression level of mRNA or protein of the GPCR polynucleotide of the present invention.

It is yet another object of the present invention to provide a kit for the diagnosis of cancer, comprising the composition.

It is still yet a further object of the present invention to provide a method for detecting the GPCR polypeptide of the present invention and a gene encoding the polypeptide.

It is still yet another object of the present invention to provide a composition for the treatment and prevention of cancer, comprising an oligonucleotide inhibiting the expression of a gene encoding the GPCR polypeptide of the present invention or an antibody against the GPCR protein of the present invention.

It is an additional object of the present invention to provide a method for screening a modulator of the GPCR protein of the present invention or a cancer therapeutic agent, comprising treating a cell expressing the GPCR protein of the present invention with a candidate compound, and determining an increase or decrease in the GPCR-mediated signal transduction activity of the protein.

Advantageous Effects

The inventive GPCR gene and GPCR protein, whose function was first identified by the present inventors, can be used as targets to suppress cancer metastasis or the cancer itself. Also, the gene or the polypeptide encoded by the gene can be used to diagnose the onset of cancer. Thus, the use of an antisense, siRNA or shRNA in silencing the novel GPCR gene of the present invention is anticipated to treat or prevent the onset or metastasis of cancer. Further, a vector carrying the gene, a transformed cell harboring the vector, and a transgenic animal with the gene may be used to scrutinize the function of the GPCR gene and be utilized as cancer models.

DESCRIPTION OF DRAWINGS

FIG. 1 shows alternative transcription variants of the novel GPCR gene (human hstm1 gene) isoforms 1 and 2 (A), expression levels of the novel GPCR gene (hstm1 gene) in various human tissues as measured by RT-PCR (B), and relative expression levels of the novel GPCR gene (hstm1 gene) in various human tissue (C).

FIG. 2C is a graph showing changes in the expression level of the GPCR gene (hstm1 gene) in non-tumor and tumor tissues of stomach cancer patients as measured by real-time PCR.

FIG. 7A shows transcription levels of IGF-I and IGF-II, which induce higher cell growth responses in normal cells overexpressing the GPCR gene (hstm1 gene) than in the control, and expression levels of the downstream factor cyclin D1. FIG. 7B shows Western blots after immune-protection assay for determining cell growth in which normal cells overexpressing the GPCR gene (hstm1 gene) are treated with anti-IGF-I and/or anti-IGF-II antibody to inhibit the signal transduction induced by the growth factors IGF. FIG. 7C are photographs showing cell growth after treatment with anti-IGF-I and/or anti-IGF-II antibody. FIG. 7D is a graph showing quantitative WST assay results for cell growth after treatment with anti-IGF-I and/or anti-IGF-II antibody.

FIG. 8A shows an in vitro binding assay result in which a G-protein coupled with the GPCR protein is identified using an His-tagged GPCR protein (His-tagged hstm1 protein) overexpressed in *E. coli*. FIG. 8B shows co-immunoprecipitation assay using flag-tagged GPCR (flag-tagged hstm1) in cells transiently overexpressing the GPCR gene (hstm1 gene). FIGS. 8C and 8D show changes in cyclin D1 proteins and Gαi1, 2, 3 mRNAs as measured by RNA interference (Gαi1, 2, 3 siRNA).

FIG. 9 shows the inhibitory effect of GPCR siRNA (hstm1 siRNA) on the cell growth of stomach cancer cells (A) and liver cancer cells (B). FIG. 9C is a graph showing the inhibitory effect of GPCR siRNA (hstm1 siRNA) on the cell growth of stomach and liver cancer cells.

FIG. 10A shows the motility of normal cells stably overexpressing the GPCR gene (hstm1 gene). FIG. 10B shows the metastastic ability of normal cells overexpressing the GPCR (hstm1 gene) qualitatively in a graph.

BEST MODE

Figure 2:
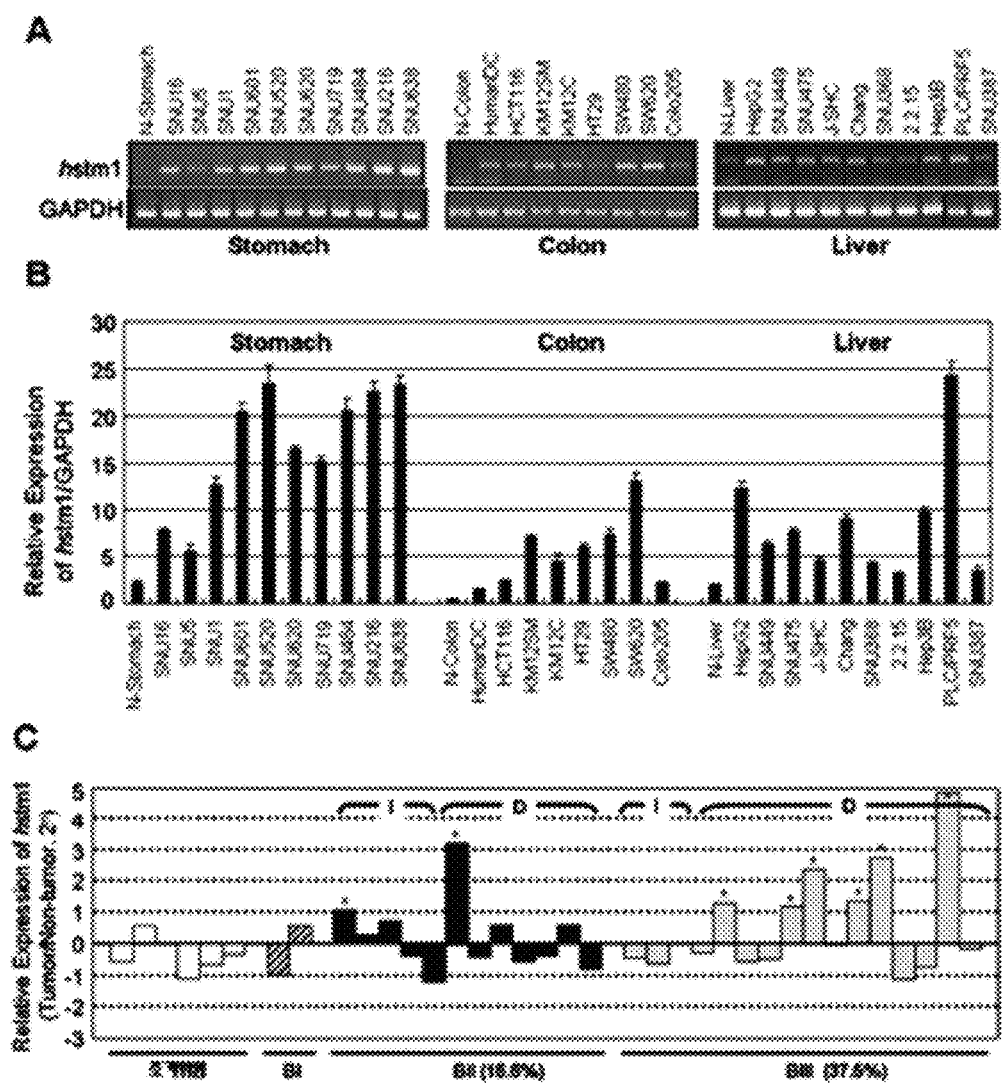
FIG. 2 shows relative expression levels of the GPCR gene (hstm1 gene) in cell lines of representative digestive organs and related organs as measured by RT-PCR (A) and as measured by real-time PCR (B).

In accordance with an aspect thereof, the present invention relates to a GPCR (G Protein Coupled Receptor) polypeptide having the amino acid sequence of SEQ ID NO: 1 or 2.

The novel GPCR polypeptide of the present invention (hereinafter referred to as "the inventive GPCR polypeptide" or "the inventive GPCR protein") has the amino acid sequence of SEQ ID NO: 1 or 2, which is translated from the transcripts having the nucleotide sequence of SEQ ID NO: 3, 4 or 5. The present inventors identified that the polypeptide is GPCR and exists in two isoforms, with translation from three transcriptional variants thereof. Also, the aberrant overexpression of the inventive GPCR polypeptide was observed to induce cancer, and thus the polypeptide of the present invention can be used as a target for treating cancer or suppressing cancer metastasis.

Preferably, the inventive GPCR protein encompasses the entire polypeptide or a fragment thereof. The fragment comprises at least 10, 20, 30 or 40 amino acid residues, preferably at least 50 amino acid residues, more preferably at least 75 amino acid residues, even more preferably at least 100 amino acid residues, and most preferably at least 150 amino acid residues, and shares a homology of at least 50%, preferably at least 60%, 70% or 80%, more preferably at least 90%, even more preferably at least 95% and most preferably at least 98% with the amino acid sequence of SEQ ID NO: 1 or 2. Also, the inventive GPCR protein is preferably comprised of the amino acid sequence of SEQ ID NO: 1 or 2. The level of expression in normal human tissues of these proteins is quite various. Isoform 1 is abundantly found in the testes and the lung but exists at a decreased level in the thymus, the bone marrow and the pancreas and at a much lower level in the small intestine, the heart and the prostate, compared to other tissues (FIGS. 1B and 1C). In contrast, the expression level of isoform 2 is observed to be higher in the testes, the pancreas, the small intestine and the prostate compared to other tissues.

In accordance with another aspect thereof, the present invention relates to a polynucleotide encoding the GPCR polypeptide.

A polynucleotide encoding the inventive GPCR protein (hereinafter referred to as "the inventive GPCR polynucleotide" or "the inventive GPCR gene"), found in the human genome, was first functionally identified by the present inventors. The polynucleotide is located at 1p36.13 on human chromosome 1 and has many alternative transcripts. The sequences of the transcripts are disclosed in SEQ ID NOS: 3, 4 and 5. The polynucleotides of SEQ ID NOS: 3, 4 and 5 are cDNAs with untranslated regions, and the longest transcript is composed of about 2279 nucleotides. Isoforms 1 and 2, translated from the three transcripts, are about 30 kDa and 23 kDa proteins, respectively, before post-translational modification. Isoform 2 lacks 65 N-terminal amino acids of isoform 1. The polynucleotides are novel genes that encode these two protein isoforms that function as GPCR (G-protein coupled receptor). The proteins do not belong to any of the GPCR classes known thus far, that is to say, orphan GPCRs. These receptors contain a PQ motif (critical for the localization of cystinosin to lysosomes).

The inventive GPCR polynucleotide encompasses all of the polynucleotide sequences encoding the novel GPCR polypeptide of the present invention. It is readily understood to those skilled in the art that various modifications may be made in the sequence of the polynucleotide of the present invention to the extent that they do not change the amino acid sequence of the polypeptide translated from the coding region, due to codon degeneracy or in consideration of the codons preferred by the organism in which they are to be expressed. Also, various modifications or alterations may be introduced even in regions other than the coding region so long as they have no influence on the expression of the gene. That is to say, the polynucleotide of the present invention may be modified as long as the resulting polynucleotides have identical or functionally equivalent biological activity, and they are also within the scope of the present invention. Therefore, a variant of the inventive GPCR polynucleotide which can be encompassed by the present invention shares a nucleotide sequence homology of at least 70%, preferably at least 80%, more preferably at least 90% and most preferably at least 95% with the nucleotide sequence of SEQ ID NO: 3, 4 or 5.

Contemplated in accordance with another aspect of the present invention is a recombinant vector carrying the polynucleotide or its fragment.

The term "vector," as used herein, refers to an expression vector that can express a protein of interest in a suitable host cell. In this context, the vector is a gene construct in which essential regulatory elements are operably linked together to express a gene of insert. Preferably, a recombinant vector is constructed to carry a polynucleotide encoding the inventive GPCR protein, or its fragment. The recombinant vector may be transformed or transfected into a host cell.

Also, the recombinant vector may be made by ligating (inserting) the gene of the present invention into a suitable vector. No particular limitations are imparted to the vector to which the gene of the present invention is to be inserted so long as it can be replicated within a host. For example, plasmid DNA or phage DNA may be employed. Examples of the plasmid DNA useful in the present invention include commercially available plasmids such as pcDNA3.1+ (Invitrogen), and pYG601BR322, pBR325, pUC118, pUC119, pUB110, pTP5, YEp13, YEp24, YCp50, Charon4A, Charon21A, EMBL3, EMBL4, gt10, gt11, and ZAP. Also, animal viruses such as retrovirus, adenovirus and vaccinia virus, and insect viruses such as baculovirus may be used, but these examples are not intended to limit the scope of the present invention.

In addition, the gene of the present invention may be introduced into a vector by digesting a purified DNA with a suitable restriction enzyme and inserting the digest to a restriction site or a cloning site of the vector DNA. In order to be operably linked with the gene of the present invention, the vector may further comprise a cis element such as an enhancer, a splicing signal, a poly A addition signal, a selection maker, and a ribosome binding sequence (SD sequence) in addition to the gene of the present invention and a promoter.

In accordance with another aspect thereof, the present invention relates to a host cell transformed with the vector.

The constructed vector may be introduced into a host cell by transformation (or transfection). Any method may be used to carry out the transformation. Typical transformation methods include CaCl$_2$ precipitation, a Hanahan method in which the effect of CaCl$_2$ precipitation is improved in combination with DMSO (dimethyl sulfoxide), electroporation, calcium phosphate precipitation, protoplast fusion, silicon carbide fiber-mediated transformation, *agrobacterium*-mediated transformation, PEG-mediated transformation, dextran sulfate, lipofectamine, and desiccation/tolerant-mediated transformation.

Using the vector or by means of transfection using the same, a gene encoding the inventive GPCR protein can be introduced into a host cell.

So long as it allows the gene of the present invention to be expressed therein, any host cell can be used without limitation in the present invention. It is also apparent to those skilled in the art that the oncogene of the present invention is used to establish a cancer cell line which can proliferate continuously. In a preferred embodiment of the present invention, a vector carrying the inventive GPCR gene is transfected into NIH3T3 cells to establish a cell line which overexpresses the inventive GPCR protein transiently or stably.

In accordance with another aspect thereof, the present invention relates to a transgenic animal obtained by implanting a host cell transformed with the vector in the womb of a surrogate mother.

As used herein, the term "transgenic animal" refers to an animal whose genotype or phenotype is at least partially altered as a result of the artificial insertion of a foreign polynucleotide sequence encoding the novel GPCR polypeptide into the genome of the animal through recombination. Examples of animals available for the creation of transgenic animals include mammals such as mice, rats, rabbits, pigs, etc., and birds, but are not limited thereto. A polypeptide encoding the inventive GPCR protein may be preferably introduced into a fertilized egg before it reaches the stage of an 8-cell embryo. The resulting transgenic animal may be used as an animal model expressing the gene, for example, a disease model to be used in screening agents for controlling, promoting or suppressing the expression of oncogenes, or anticancer agents.

So long as it is known in the art, any method may be used to prepare fertilized eggs useful for the creation of transgenic animals. Examples of the method include microinjection technique, a stem cell insertion technique, a retrovirus insertion technique, and sperm-mediated gene transfer technique, but are not limited thereto.

Then, the transformed, fertilized egg may be implanted into the womb of a surrogate mother to generate a transgenic animal.

In accordance with another aspect thereof, the present invention relates to a composition for detecting a cancer marker, comprising an agent capable of measuring the expression of the inventive GPCR gene at an mRNA level or a protein level.

As used herein, the terms "marker" or "diagnosis marker" are intended to indicate a substance capable of diagnosing cancer by distinguishing cancer cells or a subject suffering from cancer from normal cells or subjects, and includes organic biological molecules, quantities of which are increased or decreased in cancer cells or subjects relative to normal cells, such as polypeptides, proteins or nucleic acids (e.g., mRNA, etc.), lipids, glycolipids, glycoproteins and sugars (monosaccharides, disaccharides, oligosaccharides, etc.). With respect to the objects of the present invention, the diagnosis marker of cancer is the novel GPCR polypeptide or a polynucleotide encoding the same, which are specifically expressed at high levels in cancer cells, relative to normal cells or tissues.

The term "measurement of mRNA expression levels" or the corresponding phrases, as used herein, are intended to refer to a process of assessing the presence and expression levels of mRNA of cancer marker genes in biological samples to diagnose cancer, in which the amount of mRNA is measured. Analysis methods for measuring mRNA levels include, but are not limited to, RT-PCR, competitive RT-PCR, real-time RT-PCR, RNase protection assay (RPA), Northern blotting and DNA chip assay.

The phrase "measurement of protein expression levels" or related phrases, as used herein, are intended to refer to a process of assessing the presence and expression level of proteins expressed from cancer marker genes in biological samples to diagnose cancer, in which the amount of protein products of the marker genes is measured using antibodies specifically binding to the proteins. Analysis methods for measuring protein levels include, but are not limited to, Western blotting, enzyme linked immunosorbent assay (ELISA), radioimmunoassay (RIA), radioimmunodiffusion, Ouchterlony immunodiffusion, rocket immunoelectrophoresis, immunohistostaining, immunoprecipitation assay, complement fixation assay, FACS, and protein chip assay.

The agent for measuring mRNA levels may be exemplified by a pair of primers, probes, or antisense nucleotides, which correspond to the inventive GPCR polynucleotide or its fragments. The primers, probes, or antisense nucleotide sequences may be easily designed by those skilled in the art depending on the polynucleotide sequence of the present invention. Preferable are the primer sequences disclosed in SEQ ID NOS: 8 and 9.

As used herein, the term "primer" refers to a short nucleic acid strand having a free 3' hydroxyl group, which forms a base pair with a complementary template so as to serve as a starting point for the replication of the template strand. DNA synthesis or replication requires a suitable buffer, proper temperatures, polymerizing enzymes (DNA polymerase, or reverse transcriptase), and four kinds of nucleoside triphosphates, in addition to primers. In the present invention, sense and antisense primers specific for the GPCR polynucleotide can be used for PCR amplification so that the PCR products can be used to diagnose cancer. The length of the sense and antisense primers, and the PCR condition may be suitably altered depending on the information known in the art.

The term "probe", as used herein, is intended to refer to a fragment of a oligonucleotide, such as RNA or DNA, ranging in length from as short as less than 10 bases to as long as hundreds of bases, which can bind specifically to an mRNA of interest and which is tagged with a label for detecting the mRNA of interest. The probe useful in the present invention may be constructed in the form of oligonucleotide probes, single-stranded DNA probes, double-stranded DNA probes, or RNA probes. In an embodiment of the present invention, the diagnosis of cancer may be achieved by determining whether a probe complementary to the inventive GPCR polynucleotide hybridizes with a nucleotide sequence of interest. Selection of suitable probes and hybridization conditions may be modified according to information known in the art.

The primers or probes useful in the present invention may be chemically synthesized using a phosphoamidite solid support method or other well-known techniques. Their nucleotide sequences may be modified using various means known in the art. Illustrative, non-limiting examples of the modification include methylation, capping, substitution of natural nucleotides with one or more homologues, and alternation between nucleotides, such as uncharged linkers (e.g., methyl phosphonate, phosphotriester, phosphoroamidate, carbamate, etc.) or charged linkers (e.g., phosphorothioate, phosphorodithioate, etc.).

Preferably, the primer or probe preferably contains 8 or more nucleotides. Hybridization may be achieved by exposing or contacting the primer or probe to the inventive GPCR polynucleotide. Preferably, these sequences are hybridized with each other under such a stringent condition as to minimize non-specific pairings. In order to detect sequences which share 80% to 90% homology with the inventive GPCR polynucleotide, for example, a hybridization condition may include hybridizing overnight at 42° C. in a buffer containing 0.25M Na$_2$HPO$_4$, pH 7.2, 6.5% SDS, and 10% dextran sulfate and finally washing at 55° C. with a solution containing 0.1×SSC and 0.1% SDS. A stringent condition suitable for detecting a sequence which shares 90% homology with the GPCR polynucleotide of the present invention comprises hybridizing overnight at 65° C. in 0.25M Na$_2$HPO$_4$, pH 7.2, 6.5% SDS, 10% dextran sulfate, and finally washing at 60° C. with a solution containing 0.1×SSC and 0.1% SDS.

The agent capable of measuring the level of the inventive GPCR protein is preferably an antibody. The term "antibody", as used herein, refers to a specific protein molecule that directs an antigenic region. With respect to the objects of the present invention, the antibody binds specifically to the marker of the present invention, that is, the GPCR polypeptide. This antibody can be produced from a protein which is encoded by the marker gene cloned typically into an expression vector, using a conventional method. Also, partial peptides producible from the protein encoded by the marker gene fall within the scope of the antibody. For functioning as an antibody, the partial peptide may contain at least 7 amino acid residues, preferably 9 or more amino acid residues, and more preferably 12 or more amino acid residues. No particular limitations are imparted to the form of the antibodies of the present invention. Among them are polyclonal antibodies, monoclonal antibodies and fragments thereof which contain a paratope, and all immunoglobulin antibodies. Further, special antibodies such as humanized antibodies are also within the scope of the present invention. Consequently, as long as it may be produced using a method known in the art, any antibody against the inventive GPCR protein can be used in the present invention. Preferably, the antibody peptide has the sequence of SEQ ID NO.: 6 or 7.

In addition, the antibodies of the present invention which are used to detect the marker diagnostic of cancer include functional fragments of antibody molecules as well as complete forms having two full-length light chains and two full-length heavy chains. The functional fragments of antibody molecules refer to fragments retaining at least an antigen-binding function, and include Fab, F(ab'), F(ab')2, Fv and the like.

As used herein, the term "cancer" refers to a class of diseases in connection with the regulation of cell death, in which a group of cells display uncontrolled overgrowth, resulting from insufficient apoptosis. The excessively growing cells invade adjacent tissues and organs to destroy and deform normal structures, forming a tumoral mass, the state of which is defined as cancer. As a rule, a tumor is a neoplasm or a solid lesion formed by an abnormal excessive growth of cells. A tumor may be benign or malignant. Malignant tumors, which typically grow far faster than do benign tumors, invade adjacent tissues and sometimes metastasize, threatening life. The malignant tumor is typically regarded as cancer. Examples of the cancers detectable with the composition for detecting a cancer marker in accordance with the present invention include cephaloma, head and neck cancer, lung cancer, breast cancer, thymoma, mesothelioma, esophageal cancer, pancreatic cancer, colon cancer, liver cancer, stomach cancer, cholangiocarcinoma, kidney cancer, bladder, prostate cancer, testicular cancer, spermocytoma, ovarian cancer, uterine cervical cancer, endometrial cancer, lymphoma, acute leukemia, chromic leukemia, multiple myeloma, sarcoma, and malignant melanoma, but are not limited thereto. The composition for detecting a cancer marker is used for a diagnosis of cancer. In a preferred embodiment of the present invention, the composition for detecting a cancer marker is applied to stomach cancer, colon cancer and liver cancer cell lines and to subjects suffering from these cancers to examine the expression level of the cancer marker therein. When the composition was applied, the GPCR protein was observed to have a remarkably higher expression level in tissues from subjects with cancer than in those from normal subjects.

The term "metastatic cancer" is intended to describe the property of cancer and refers to a carcinoma metastasized from the originating site of cancer to another site through blood vessels or lymph ducts. Fundamental treatment of cancer requires controlling the metastasis site of cancer as well as treating primary cancer. Examples of metastatic cancers include colorectal cancer, prostate cancer, gynecologic cancer, stomach cancer, multiple myeloma, liver cancer, lung cancer, pancreatic cancer, thyroid cancer, kidney cancer, cholangiocarcinoma, gallbladder cancer, neuroblastoma, and Hodgkin lymphoma, which are known to metastasize through blood stream. Particularly, breast cancer, a kind of gynecologic cancer, prostate cancer, lung cancer, and colorectal cancer are apt to metastasize to the bone and the liver. The examples of metastatic cancer are within the scope of the present invention. No particular limitations are imparted to the cancer if it allows the spread of tumor. Isoform 2 of the GPCR protein of the present invention is observed to show increased expression levels particularly in metastatic cancers. Thus, isoform 2 can be utilized as a marker for diagnosing metastatic cancer. The suppression of the expression of isoform 2 may result in preventing or treating metastatic cancer as well as primary cancer.

In accordance with another aspect thereof, the present invention provides a cancer diagnosis kit that comprises the composition.

The term "diagnosis," in the context of the present invention, refers to a process of determining the presence or absence of the GPCR polypeptide or polynucleotide of the present invention in a biological specimen or a tissue sample so as to identify the existence or characteristics of a disease related to the expression of the gene.

The detection of the cancer marker may be accomplished by determining the expression level of the GPCR polypeptide or a polynucleotide encoding it using the kit of the present invention. The kit of the present invention may comprise a primer or probe for measuring the expression level of the cancer diagnosis marker, an antibody selectively recognizing the cancer marker or its fragments retaining an antigen-binding function, and/or one or more agents, devices or compositions suitable for the analysis of the polypeptide or polynucleotide. For example, the diagnosis kit for the quantitative analysis of the polynucleotide or gene of the present invention may comprise at least one oligonucleotide specifically binding to a polynucleotide encoding the GPCR polypeptide. In a preferable embodiment, the diagnosis kit of the present invention may include a pair of primers specific for the nucleotide sequence of SEQ ID NO: 3, 4 or 5, reverse transcriptase, Taq polymerase, PCR primers, and dNTP. As long as it takes advantage of analysis methods known in the context of "measurement of mRNA expression level", any kit may be employed without limitations.

In another preferable embodiment, the cancer diagnosis kit of the present invention may comprise an antibody specifically binding to the inventive GPCR protein. As long as it takes advantage of analysis methods known in the context of "measurement of protein expression level", any kit may be employed without limitations. Preferable is an ELISA kit or a protein chip kit.

The measurement of protein expression level using an antibody is based on the formation of an antigen-antibody complex between the GPCR protein and an antibody thereto. The amount of the antigen-antibody can be measured using various methods, resulting in a determination of the protein expression level.

As used herein, the term "antigen-antibody complex" is intended to refer to a product formed by the binding of a cancer marker protein to an antibody specific thereto. The antigen-antibody complex thus formed may be quantitatively determined by measuring the signal size of a detection label.

For instance, cancer can be diagnosed by determining a significant increase in GPCR protein expression level in a suspected subject from the comparison of the amount of antibody-antigen complex between the suspected subject and a normal control. In this regard, a sample from a subject suspected of having cancer is treated with an antibody specific for the inventive GPCR protein to form an antigen-antibody complex which can be quantitatively analyzed using a kit on the basis of an ELISA assay, an RIA assay, a sandwich ELISA assay, a Western blotting assay, a radioimmunodiffusion assay, an ouchterlony immunodiffusion assay, a rocket immunoelectrophoresis assay, an immunohistostaining assay, an immunoprecipitation assay, a complement fixation assay, FACS, a protein chip assay or an immunodot assay. Comparison of the analysis data with those of a normal subject allows the diagnosis of cancer in connection with an increase in GPCR protein expression.

In accordance with a further aspect thereof, the present invention pertains to a method for detecting the GPCR polypeptide of the present invention or a polynucleotide encoding the same.

In detail, the expression of a gene may be detected at the mRNA or the protein level. Isolation of the mRNA or protein from a biological specimen may be achieved using a well-known method.

As used herein, the term "biological specimen" refers to a sample from which the expression level of a gene or protein of GPCR can be measured. Examples of the biological specimen useful in the present invention include tissues, cells, whole blood, serum, plasma, saliva, sputum, cerebrospinal fluid and urine, but are not limited thereto.

In an embodiment of the method of detecting according to the present invention, the expression level of a gene in a subject suspected of having cancer can be compared to that of a normal control to diagnose cancer incidence in the subject. More specifically, what is measured is the expression level of the marker of the present invention present in a biological sample from a subject suspected of having cancer. This level is compared with that measured in a biological sample from a normal control. When the expression level of the marker of the present invention is higher in the subject than in the normal control, the subject may be determined to be affected by cancer.

In the case where a polynucleotide encoding the GPCR polypeptide of the present invention is used as a marker, the method comprises (a) preparing a biological specimen; (b) treating the biological specimen with an agent used to measure an mRNA level of GPCR; (c) detecting a complex between the agent and a polynucleotide complementary to the agent; and (d) quantitatively comparing the complex between a subject and a normal control. In the case where the GPCR polypeptide of the present invention is used as a marker, the method comprises (a) preparing a biological specimen; (b) treating the biological specimen with an antibody specific for the inventive GPCR protein; (c) detecting an antigen-antibody complex; and (d) quantitatively comparing the complex between a subject and a normal control.

In accordance with still a further aspect thereof, the present invention pertains to a composition for the treatment and prevention of cancer, comprising as an active ingredient an oligonucleotide inhibiting the expression of the inventive GPCR gene or an antibody inhibiting the activity of a GPCR polypeptide.

In order to determine the tumorigenicity of the novel GPCR gene or protein of the present invention, observations were made of the contact inhibition and anchorage independent growth in an NIH3T3 cell line expressing the gene. The observations showed an insensitivity in contact inhibition and an increase in anhorage independent growth of the cell line in which the GPCR gene of the present invention was stably expressed. In addition, injection of a vector carrying the GPCR gene of the present invention into immunity-devoid nude mice induced the formation of a tumor.

In a preferred embodiment of this aspect, the composition may include a substance inhibiting the expression of the GPCR polynucleotide of the present invention. The GPCR expression inhibitor substance may be selected from the group consisting of siRNA, shRNA, an aptamer and an antisense oligonucleotide. Preferable is the oligonucleotide selected from the group consisting of SEQ ID NOS: 20 to 23, SEQ ID NOS: 36 to 51, and a combination thereof.

As used herein, the term "siRNA (small interfering RNA)" is intended to refer to a small nucleic acid molecule of about nucleotides, which mediates RNA interference or gene silencing. When siRNA is introduced into a cell, it is recognized by dicer to degrade the gene encoding the GPCR polypeptide, resulting in the specific knockdown of a GPCR gene.

The term "shRNA" refers to a short hairpin RNA in which sense and antisense sequences of an siRNA target sequence are separated by a loop structure of 5 to 9 bases.

Recently, the phenomenon of RNA interference (RNAi) has been studied for its application to a method for controlling protein expression at the gene level. Typically, siRNA has been shown to inhibit protein expression by binding specifically to mRNA, having a sequence complementary to a target gene.

In order to interfere with the expression of oncogenes or metastagenes, the composition comprising siRNA or shRNA according to the present invention may be administered to a subject according to a typical method adopted for use in gene therapy based on these RNAs. For instance, gene expression can be regulated by low-volume intravenous injection of siRNAs according to the method described by Filleur et al., Cancer Res., 63(14): 3919-22, 2003. In order to increase the cellular uptake and stability of siRNAs, siRNA may also be injected in the form of a conjugate according to Chien et al., Cancer Gene Ther., 12(3) 321-8, 2005.

The short interfering RNA molecules (siRNA) contained in the present composition can be prepared by direct chemical synthesis (Sui G et. al, (2002) *Proc Natl Acad Sci* USA 99:5515-5520) or in vitro transcription (Brummelkamp T R et al., (2002) *Science* 296:550-553), but the present invention is not limited to these methods. Also, shRNAs, which are designed to overcome the drawbacks of siRNAs, including expensive siRNA biosynthesis and low transfection efficiency, so that the shRNAs cause the short-term persistence of an RNA interference effect, can be expressed from a RNA polymerase-based promoter contained in an adenoviral, rentiviral or plasmid expression vector system, that has been introduced into cells. The shRNA molecules are processed to functional siRNA molecules using an siRNA processing enzyme (Dicer or RNase) within the cells, and then induce the silencing of a target gene.

As used herein, the term "antisense" is intended to refer to an oligomer having a sequence of nucleotide bases and a subunit-to-subunit backbone that allows the antisense oligomer to hybridize with a target sequence in RNA by Watson-Crick base pairing to form an RNA:oligomer heteroduplex within the target sequence, typically with mRNA. The oligomer may have exact sequence complementarity to the target sequence, or near complementarity thereto. These antisense oligomers may block or inhibit the translation of the mRNA, and/or modify the processing of mRNA to produce a splice variant of the mRNA. Thus, the antisense oligomer of the present invention is an antisense oligomer complementary to a polynucleotide encoding the GPCR polypeptide. For gene therapy, the antisense oligonucleotide according to the present invention may be administered by a typical method. The administration of the composition may lead to preventing or suppressing oncogene expression. For instance, an antisense oligodeoxynucleotide is loaded onto a microparticle carrier based on poly-L-lysine by electrostatic attraction as described in J. S. Kim et al., J controlled Release 53, 175-182 (1998) and the oligonucleotide-loaded microparticle is injected intravenously, but the present invention is not limited to this method.

Preferably, the composition according to the present invention may include a known therapeutic agent, which is directly or indirectly conjugated to the agent or is present in an unconjugated form. The therapeutic agent capable of binding to the antibody includes, but is not limited to, radionuclides, drugs, lymphokines, toxins and bispecific antibodies. As long as it can exert therapeutic effects on cancer when conjugated to an antibody or can be administered in combination with an siRNA, an shRNA or an antisense oligonucleotide, any known therapeutic agent can be used in the present invention.

Examples of the radionuclides include, but are not limited to, $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

The drugs and toxins useful in the present invention include, but are not limited to, etoposide, teniposide, adriamycin, daunomycin, caminomycin, aminopterin, dactinomycin, mitomycin, cis-platinum and cis-platinum analogues, bleomycins, esperamicins, 5-fluorouracil, melphalan, and nitrogen mustard.

In a preferred embodiment thereof, the composition of the present invention may be a composition suppressive of the growth or metastasis of cancer, comprising a substance inhibiting the activity or expression of the GPCR protein. Preferably, the activity-inhibiting substance is an antibody that specifically recognizes the GPCR protein. The antibody includes all monoclonal antibodies and chimeric antibodies, humanized antibodies and human antibodies thereof. As long as they have the binding property of specifically recognizing GPCR, the antibodies include complete forms having two full-length light chains and two full-length heavy chains, or may be in the form of functional fragments of antibody molecules. As used herein, the term "functional fragments of antibody molecules" is intended to refer to fragments retaining at least an antigen-binding function, which are exemplified by Fab, F(ab'), F(ab')$_2$ and Fv.

Preferably, the composition according to the present invention may include an acceptable carrier appropriate to the administration mode thereof.

The active ingredient may be combined with pharmaceutically acceptable vehicles, excipients, or additives. Examples of the pharmaceutically acceptable carriers useful in the present invention include physiological saline, sterile water, Ringer's solution, buffered saline, dextrose solution, maltodextrin solution, glycerol, ethanol, and liposomes. They may be used alone or in combination. If necessary, the composition may further comprise other typical additives such as antioxidants, buffers, etc. Depending on the mode of administration, the composition may be formulated with a diluent, a dispersant, a surfactant, a binder and/or a lubricant into an injection dosage form such as an aqueous solution, suspension, emulsion, etc. or an oral dosage form such as pill, capsule, granule, tablet, etc. When conjugated with the carrier, an antibody or ligand specific to the target organs or tissues may direct the active ingredient toward the organs or tissues. Typical vehicles, excipients and additives known in the art may be used in the present invention. The present invention is not limited to the examples of vehicles, excipients and additives.

The composition or formulation may be administered in a therapeutically effective amount to subjects through a suitable route according to purpose and necessity. The pharmaceutical composition may be administered orally, parenterally, subcutaneously, intraperitoneally, or intranasally. For local immunosuppressive therapy, the composition may, if desired, be administered using a suitable method, including intralesional administration. Parenteral injections include intramuscular, intravenous, intraarterial, intraperitoneal and subcutaneous routes. The therapeutically effective amount of the composition comprising the antisense oligonucleotide, shRNA or shRNA may vary depending on various factors well known in the medical art, including the kind and degree of the response to be achieved, the patient's age, body weight, state of health, etc.

In accordance with still yet another aspect thereof, the present invention is directed to a method for screening a modulator of the GPCR protein of the present invention, comprising treating a cell expressing the inventive GPCR protein with a candidate compound and measuring GPCR-mediated signal transduction activity in the cell.

If necessary, the cells expressing the inventive GPCR protein may be suitably selected using the above-illustrated recombinant vector, host cells transformed with the vector, or transgenic animals harboring the gene. After a candidate compound predicted to be associated with GPCR-mediated signal transduction activity is applied to the cells, it is possible to determine whether the candidate compound functions as a modulator of the inventive GPCR protein. For example, if the candidate compound induces an increase in GPCR-mediated signal transduction activity, it is determined to be an agonist of the inventive GPCR protein. In contrast, when the GPCR-mediated signal transduction activity is reduced thereby, the candidate compound is determined to be an antagonist.

The term "agonist," as used herein, is intended to refer to a molecule that binds to a receptor to significantly induce, improve or enhance the biological activity or activation of the receptor for a ligand, directly or indirectly. With respect to the purpose of the present invention, an agonist is a substance that binds to the inventive GPCR protein to induce or enhance the biological activity or activation of the receptor. As used herein, the term "antagonist" refers to a substance that shows antagonistic action. When two or more substances are used, if one decreases the effect of the other, it is called an antagonist. With respect to the purpose of the present invention, it is a substance that interacts with a ligand for the GPCR protein to decrease the effect of the ligand.

To determine whether GPCR-mediated signal transduction activity is increased or decreased, various methods including measuring the level of one or more of various proteins or compounds involved in a signal transduction pathway may be used. Preferably, an increase or decrease in GPCR-mediated signal transduction activity can be determined by measuring the level of cAMP. In a preferred embodiment, to verify external stimulant factors that have an influence on the novel GPCR protein, some substances, known as GPCR ligands, were used to examine whether the overexpression of the novel GPCR promotes cell growth. In detail, cells were treated with EGF, PDGF, insulin, IGF-1, HGF, VEGF, angiotensin II, bradykinin, LPA and PTX. PDGF, insulin, IGF-1, VEGF, angiotensin II, bradykinin, and LPA were observed to promote cell growth whereas PTX inhibited cell growth.

In accordance with still yet another aspect thereof, the present invention is directed to a method for screening a therapeutic agent for cancer, comprising treating a cell expressing the inventive GPCR protein with a candidate compound and measuring a GPCR-mediated signal transduction activity in the cell.

This screening method may be conducted in a manner similar to that of the screening method of the modulator. That is, if the candidate compound induces an increase in GPCR-mediated signal transduction activity, it is determined as one promoting oncogenesis because the expression level of the GPCR protein and gene of the present invention is increased. When it reduces the GPCR-mediated signal transduction activity, the candidate compound is determined to be a possible therapeutic agent for cancer because it can suppress the expression of the oncogenic gene and protein. According to the screening method, the activity of the candidate can be easily determined by the cAMP expression level.

A better understanding of the present invention may be obtained through the following examples which are set forth to illustrate, but are not to be construed as limiting the present invention applying limitations to it.

MODE FOR INVENTION

Example 1

Analysis of Novel GPCR

The novel orphan GPCR, overexpressed in stomach, colorectal, and liver cancer cell lines, was named hstm1 (human seven transmembrane protein 1) (hereinafter, the novel GPCR gene of the present invention is named "hstm1" and the novel GPCR protein of the present invention named "hstm1 protein" or "hSTM1". "hstm1" is used interchangeably with novel GPCR). The gene $stm1^+$ of the fission yeast S. pombe the expression level of which varies depending on external stress and level of nitrogen or saccharide, was used to detect a human homologous gene which is identified as novel orphan GPCR and named hstm1. The novel receptor gene is located at 1p36.13 on chromosome 1 and has a few alternative transcripts. Transcription variant 1 (hstm1a) (SEQ ID NO:3) is a full-length gene comprising the complete N-terminus, which codes for one of the two hstm1 isoforms. An isoform 1 of hstm1 can be formed from two different alternative splicing variants (SEQ ID NOS: 3 and 4), which are also within the scope of the present invention. Isoform 2 of hstm1 is derived from alternative splicing variant 3 (SEQ ID NO: 5), which encodes a protein lacking 65 N-terminal amino acid residues.

Example 2 mRNA Level of Novel GPCR in Normal Human Cell Tissues

Total RNA of normal total cell tissues was purchased from Clontech. Co. Total RNAs from human stomach (cat. No 636578), testis (cat. No 636533), thymus (cat. No 636549), bone marrow (cat. No 636548), brain (cat. No 636530), liver (cat. No 636531), large intestine (cat. No 636553), kidney (cat. No 636529), lung (cat. No 636524), mammary gland (cat. No 636570), ovary (cat. No 636555), heart (cat. No 636532), thyroid (cat. No 636530), pancreas (cat. No 636577), small intestine (cat. No 636539), and prostate (cat. No 636539) were used. To 1 µg of each total RNA was added 1 µl of oligo (dT)15, and this mixture was boiled at 65° C. for 10 min and allowed to cool. The mixture was combined with 1 µl of an RNase inhibitor, 4 µl of 5×RT buffer, 2 µl of dNTP, 2 µl of DTT, and 0.5 µl of RT enzyme (reverse transcriptase), and its volume was adjusted into a total of 20 µl with distilled water, followed by incubation at 42° C. for 60 min and then at 70° C. for 5 min to prepare cDNA (iNtRON Biotech).

Then, 2 µl of the prepared cDNA was mixed with 30 pmoles of each GAPDH primer and an amount of distilled water so as to form a total volume of 10 µl before the addition of 10 µl of 2× Taq premix (Hot start) for RT-PCR. PCR was performed with 22 cycles of 94° C. for 30 sec, 55° C. for 30 sec, and 72° C. for 1 min and the PCR products thus obtained were loaded onto agarose gel to measure the quantities thereof. Calibration was made such that the quantity of GAPDH PCR product was equalized across all the samples. Using the calibrated amounts, PCR was performed in the presence of hstm1 primers, with 35 cycles of the same thermal conditions. The PCR products thus obtained were loaded onto agarose gel to visualize the amount of mRNA in each tissue. The mRNA level of hstm1 in each tissue was quantified using real-time PCR (the RG-6000 of Corbett Research). For this, 2× Quantitect SYBR Green PCR Kit was purchased from Qiagen. On the basis of the mRNA level in the stomach, relatively smaller levels were detected in the heart, the pancreas, the thymus, the prostate, and the small intestine whereas comparatively higher levels were observed in the lung and the testes. Particularly, the expression level in the testes was remarkably different from that in the other tissues. The primers used in the real-time PCR are listed in Table 1, below. The GAPDH primers used for the control were purchased from Qiagen (QT00079247). Real-time PCR was performed with 40-45 cycles of 95° C. for 5 sec, 55° C. for 15 sec and 72° C. for 20 sec.

TABLE 1

|  |  | SEQUENCE | Annealing Tm | PCR PRODUCT SIZE | cycle |
|---|---|---|---|---|---|
| hstm1 F | SEQ ID NO: 8 | 5'-tctggaagaaactgggctcc-3' | 54 | 194 bp | 40 |
| hstm1 R | SEQ ID NO: 9 | 5'-catgttgcccgtcttgtagg-3' |  |  |  |

Example 3 mRNA Level of Novel GPCR in Human Gastrointestinal Cancer Cell Lines

Stomach, colorectal and liver cancer cell lines were grown in 6-well dishes containing RPMI medium supplemented with 10% fetal bovine serum and an antibiotic. After reaching 80% confluence, the cells were washed with PBS buffer and ruptured with 1 mL of TRIZOL to isolate total RNA which was then converted into cDNA and quantified for GAPDH in the same manner as in Example 2. Also, hstm1 levels were determined using RT-PCR and real-time PCR. The expression levels of hstm1 in the gastrointestinal cell lines, that is, stomach, colorectal and liver cancer cell lines, were found to be higher than in normal tissues, and were consistently higher in the stomach cancer cell lines.

Example 4

Expression Level of Novel GPCR in Clinical Samples of Stomach Cancer Patient mRNA was isolated from normal and cancerous tissue of stomach cancer patients. For this, a total RNA extraction kit (iNtRON Biotech.) was employed. In this regard, 20 mg of a stomach tissue was ruptured with 1 ml of easy-BLUE reagent and vortexed with 200 µl of chloroform before centrifugation for 10 min. In a fresh tube, 400 µl of the supernatant was mixed with 400 µl of isopropanol and incubated at room temperature for 10 min, followed by centrifugation at 13,000 rpm for 10 min to isolate RNA. The RNA pellet thus formed was washed with 75% alcohol, dried and dissolved in 50 µl of DEPC-water. After RNA quantification, 1 µg of each RNA was used to prepare cDNA in the same manner as in Example 2. While the cDNA served as a template, real-time PCR was performed using the hstm1 primers of SEQ ID NOS: 8 and 9. No significant results were obtained from the stomach cancer tissues in the early stages of stage 1 or 2, but 37% of the samples from stomach cancer tissues of stage 3 or higher showed a significant increase in the expression level of hstm1. Particularly, a higher percentage of diffuse tissues were observed to have a significant increase. In light of these facts, the expression of hstm1 was thought to be associated with the diffuse and progressive stomach cancer of stage 3 or higher.

Example 5

Transient and Permanent Transfection into NIH3T3 Cell

To further examine properties of the novel human orphan receptor hstm1, NIH3T3 cells were transiently or permanently transfected using Lipefectamine Plus.

Cell Culture and Transfection Method

NIH3T3 cells were maintained in DMEM (Gibco) supplemented with 10% heat-inactivated fetal bovine serum, 100 IU/ml penicillin G, and 100 µg/ml streptomycin sulfate. The cells were grown in various sizes of culture flasks at 37° C. in a 5% $CO_2$ atmosphere. For permanent transfection, the maintained cells were cultured in DMEM containing 400 µg/ml Geneticin (G418).

For transient transfection of NIH3T3 cells, Lipofectamine Plus (Life Technologies) was employed. One day before transfection, NIH3T3 cells were seeded into 60-mm dishes or 6-well plates, and 2 µg of DNA and 4 µl of the Plus reagent (Life Technologies) was mixed together, added to each dish or well, and incubated at room temperature for 15 min (Solution A).

To 150 µl of serum-free medium was added 6 µl of Lipofectamine Plus (Solution B). Solutions A and B were mixed together and incubated at room temperature for 15 min to form a complex. To this was added 900 µl of a serum-free medium. The cells were washed once with serum-free medium and mixed with the DNA-Lipofectamine Plus complex (a total volume of 1200 µl), followed by incubation at 37° C. for 5 hours in a 5% $CO_2$ incubator. Subsequently, the medium was removed and 3-5 ml of fresh DMEM supplemented with 10% heat-inactivated fetal bovine serum was added to the cells which were then incubated in an incubator.

The cells which were transiently transfected by the Lipofectamine Plus technique were used to establish a permanently transfected stable cell line. After the transfection, the cells were cultured to form colonies over 8-10 days, with the replacement of a fresh selective medium containing 400-1000 µg/ml Geneticin (G418) every two or three days. For additional culture and experiments, the cells were transferred to 100-mm culture dishes. Monoclonal cells were screened by a limiting dilution assay in 96-well plates. This procedure was repeated to obtain the stable cell lines separated for being monoclonal. The cells were added to a medium containing 10% DMSO and 20% serum and stored in liquid nitrogen. During experiment, care must be taken lest the number of passages of the cells reach 15.

Example 6

Assay of Novel GPCR Gene for Ability to Promote Cell Growth and Tumorigenicity Using hstm1 Stable Cell Line

Figure 3:
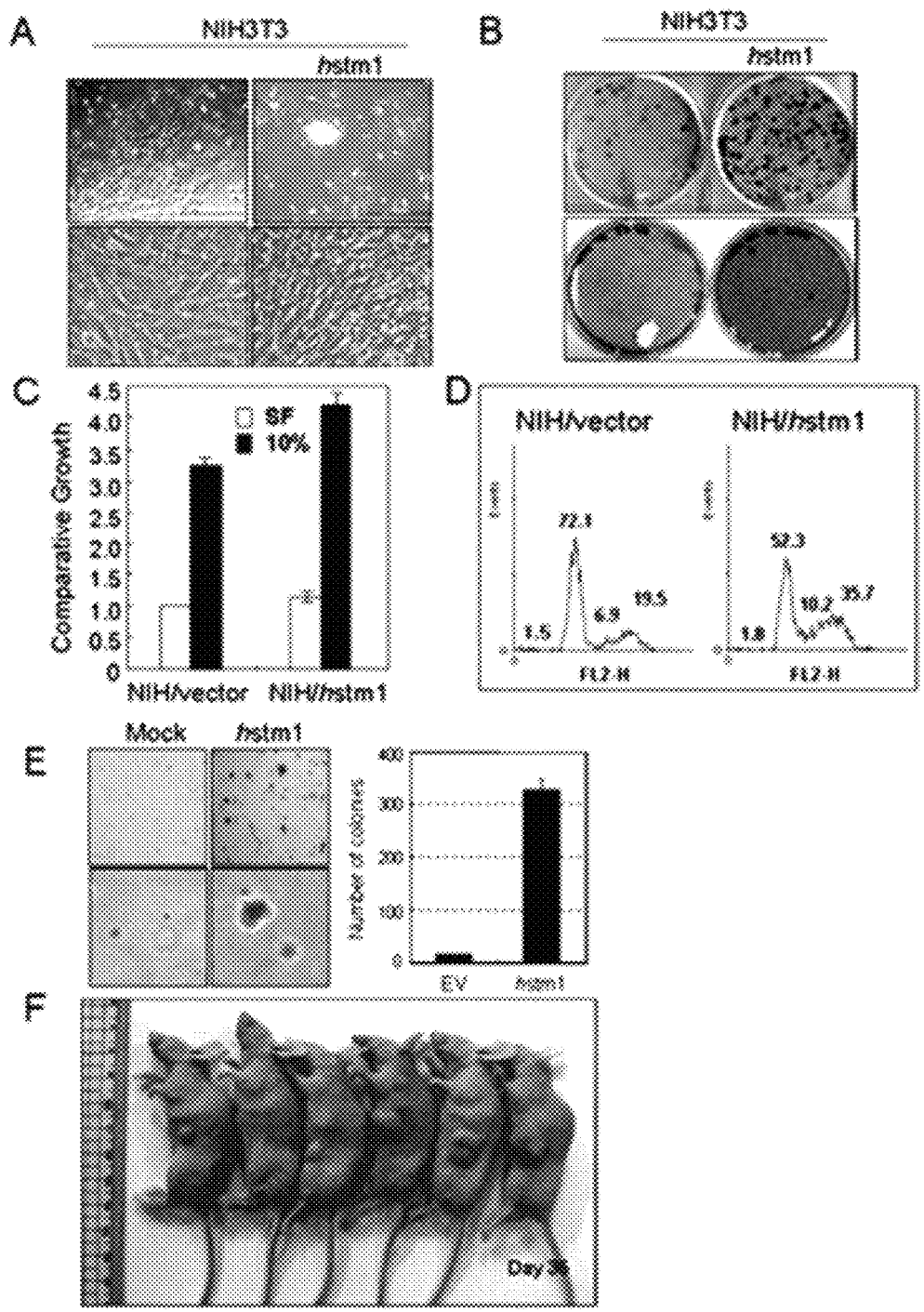
FIG. 3A shows the formation of foci of normal cells overexpressing the GPCR gene (hstm1 gene) and the insensitivity of the cells to contact inhibition.
FIG. 3B shows the growth and the formation of foci of normal cells overexpressing the GPCR gene (hstm1 gene), compared to the control, according to cell concentrations.
FIG. 3C shows higher growth rates of normal cells overexpressing the GPCR gene (hstm1 gene), compared to the control.
FIG. 3D shows the cell cycle of normal cells overexpressing the GPCR gene (hstm1 gene).
FIG. 3E shows the anchorage-independent growth of normal cells overexpressing the GPCR gene (hstm1 gene) in photographs and in a graph.
FIG. 3F shows the formation of tumor in immune deficient mice after they were subcutaneously injected with normal cells overexpressing the GPCR gene (hstm1 gene) or control cells.
Figure 4:
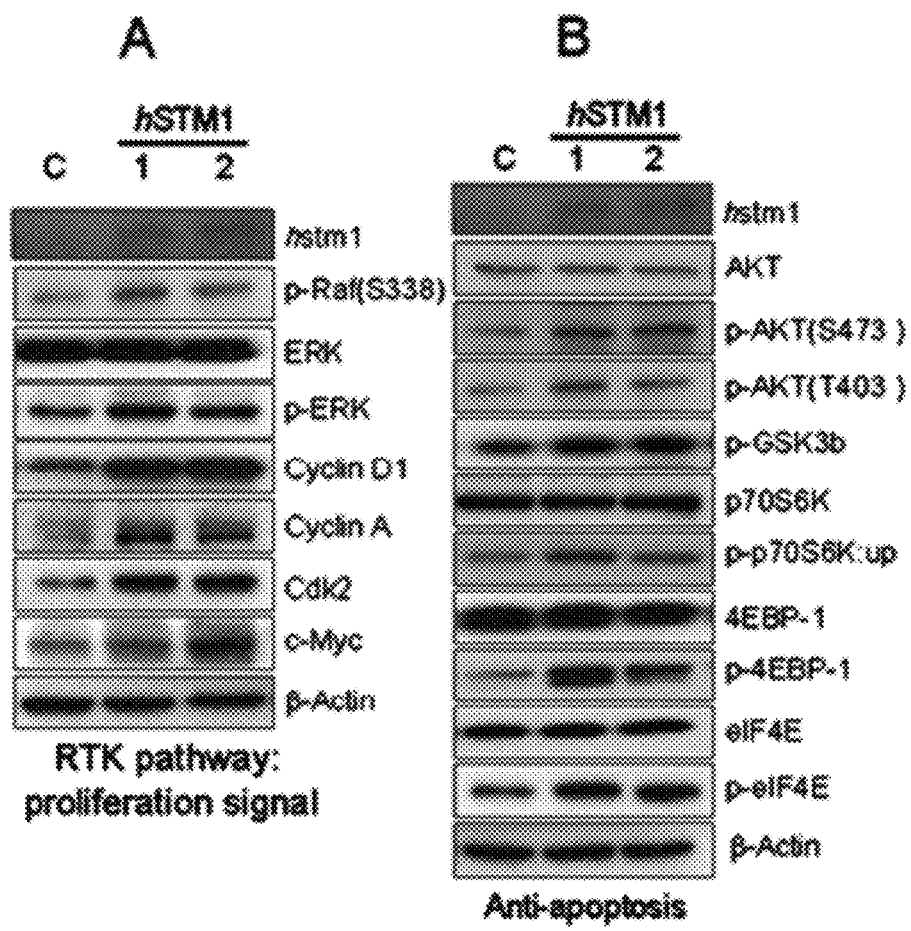
FIG. 4 shows Western blots for proteins involved in the MAP kinase pathway, which is associated with cell growth and tumor formation (A), and the anti-apoptosis pathway (B) in normal cells overexpressing the GPCR gene (hstm1 gene).

1) Observation of foci of the cell line permanently transfected with hstm1:

Cells transfected respectively with a mock vector and a vector carrying an hstm1 gene were seeded at low confluence (500 cells/dish) and observed for the formation of cell foci. Whereas the cells anchoring the mock vector grew to spread irregularly, the cells expressing hstm1 formed foci (FIGS. 3A and 3B).

2) Observation of growth inhibition of cells permanently transfected with hstm1 by contact inhibition:

Control cells and hstm1-expressing cells were seeded at high confluence ($5 \times 10^6$ cells) and cultured for 5 days with the replacement of a fresh medium every two days. As a rule, normal cells stop to grow when they are in contact with many surrounding cells. In contrast, the hstm1-expressing cells did not stop growing, but continued to proliferate densely, with the intercellular distance shortened (FIGS. 3A and 3B).

3) The control cells and the hstm1-expressing cells were counted and the same number of cells were seeded in the same number into 96-well dishes and incubated for 12 hours to attach the cells to the dishes. This time was set as T0. The amounts of the cells were determined using a WST assay (Takara, cat No. MK400, 10 µl of wst was aliquoted into each well of 96-well plates in which cells had been cultured, and after a predetermined period of time passed, the absorbance of each well was measured at a UV wavelength of 450 nm using a spectrophotometer. In this regard, the cells were cultured in a serum-free medium or 10% fetal bovine serum-supplemented medium for 24 hours. At T24, the degree of cell growth was measured by WST assay to determine T24 values relative to the T0 value. The growth rate of the cell line expressing hstm1 was compared to that of the control. In the medium free of bovine serum, the growth of cells was slightly promoted while the growth rate in the serum-supplemented medium was 30% accelerated (FIG. 3C).

4) The cells grown in the serum-supplemented medium were detached with trypsin/EDTA, fixed with alcohol for 12-24 hours, washed with PBS buffer, and then treated with RNase to degrade RNA. To these cell samples was added a DAPI solution to stain DNA, followed by observation of cell cycles by conducting FACS analysis. The hstm1-expressing cells grew fast so that a comparative abundance of cells were found to exist in G2 phase (FIG. 3D).

FACS (Fluorescent Activated Cell Sorter) Analysis

NIH3T3 cells stably transfected with the fluorescent expression vector pIRES-EGFP2(NIH3T3-IRES-EV) and the expression vector pIRES-EGFP2-hSTM1 carrying an hSTM1 gene were seeded at a cell density of $4 \times 10^5$ and $5 \times 10^5$ cells/dish into 60-mm cell culture dishes.

After incubation in DMEM growth medium supplemented with 10% FBS (Fetal Bovine Serum) and 1% antibiotics for 24 hours, the medium was replaced with a fresh one. The cell was grown to 70% confluence and then washed with 1×PBS before treatment with trypsin-EDTA. The cells thus detached were transferred to 15-ml Corning tubes, each containing 5 ml of PBS, and settled down by centrifugation. After the supernatant was discarded, the cells were thoroughly washed with 5 mL of PBS and spun down again. After removal of the supernatant, the cells were fixed and stored in 5 ml of cold 70% ethanol at −20° C. for one hour or longer. Three hours before FACS analysis, the cells were collected by centrifugation, and the supernatant was discarded and the cells were washed with 5 ml of PBS. This washing procedure was repeated two times. After centrifugation, 0.5 ml of PI (propidium iodide) staining solution was added to the cells and vigorously pipetted (PI staining solution: 3 mM sodium citrate, 50 µg/ml PI [Sigma, P4170] in PBS). To prevent the RNA from being stained, RNase A was added at a concentration of 10 µg/ml after which the samples were incubated at 4° C. for 3 hours or overnight at −20° C. The prepared samples were used in cell cycle analysis using FACS.

5) The anchorage-independent growth of the cells permanently expressing hstm1 was examined. First, a 1.8% noble agar solution was mixed at a ratio of 1:1 with a medium containing 20% bovine serum, and the mixture was aliquoted in an amount of 2.5 ml to 60-mm dishes and solidified. A suspension of $5 \times 10^4$ cells in a medium containing 20% bovine serum was mixed at a ratio of 1:1 with 0.6% noble agar and poured and solidified over the previously solidified agar in the dishes. To prevent the agar from drying, 2 ml of a medium was added, followed by incubation of the cells for about 20 days to form colonies, with the replacement of the medium with a fresh one every two days. Colonies formed were counted and revealed an increase in the anchorage-independent growth of the hstm1-expressing cells (FIG. 3E).

6) Cells transfected permanently with hstm1 or a vector alone were subcutaneously injected into immune deficient nude mice to examine the formation of tumors. After being harvested with trypsin/EDTA, the cells cultured in the culture method of Example 5 were washed twice with PBS and finally resuspended in PBS buffer. The same number of the cells was injected into the nude mice. For 35 days after injection, the formation of tumors in the mice was examined. No tumor development was observed in the immune deficient nude mice injected with NIH3T3 cells anchoring the mock vector until day 28, and of 10 mice, three developed small tumors. Of 10 mice injected with hstm1-expressing cells, nine were found to have large tumors on day 30.

Example 7

Gene Expression Induced by Overexpression of Novel GPCR Gene

To investigate the mechanism in which hstm1 overexpression promotes tumorigenesis, proteins involved in MAP kinase pathway, signaling pathways associated with cell growth, and anti-apoptosis pathway were analyzed using Western Blot. As a result, the hstm1 gene activated the MAP kinase pathway and the anti-apoptosis pathway revealing that it is involved in tumorigenesis via these pathways. Information on the antibodies used is as follows.

Western Blot Analysis

As illustrated in Example 6, the cells grown in 60-mm dishes were washed once with PBS and lyzed in chilled protein-dissolution buffer (RIPA cell lysis buffer: 50 mM Tris-Cl (pH 7.5), 150 mM NaCl, 1% Nonidet P-40, 10% Glycerol, 1 mM PMSF, 1 mM DTT, 20 mM NaF, 1 mM EDTA, Protease inhibitor) to prepare proteins of the cells. 30 µg of each protein sample was separated by 10% or 12% SDS-PAGE (sodium dodecyl sulfate polyacrylamide gel electrophoresis), and transferred onto PVDF membranes.

The filters onto which the proteins were transferred were cut into suitable sizes and treated with corresponding antibodies. Information on the antibodies is as follows: anti-hstm1 (prepared), anti-p-raf (S438. 1:1000, Cell signal #9427), anti-p-raf (S259)(1:1000, Cell signaling #9421), anti-phospho Erk1/2(1:10000, Pharmingen, 554093), anti- Erk1/2(1:3000, Santa Cruz, sc-7382), anti-Cyclin D1(1:3000, Pharmingen. 554180), anti-cyclin A (1:3000, Santa Cruz, sc-751), anti-cdk2 (1:1000, Santa Cruz, sc-6248), anti-c-myc (1:1000, Santa Cruz, sc-7890), anti-Akt (1:3000, Cell signal, #9272), anti-p-AKT(S473) (1:2000, Cell signal, #9271), anti-AKT(Thr-308) (1:2000, Cell signal, #9275), anti-p-GSK3b(1:3000, Cell signal, #9336), anti-p70S6K(1:2000, Cell signal #9202), anti-p-p70S6K(1:2000, Cell signal, #9208), anti-4EBP1 (1:3000, Cell signaling, #9452), anti-p-4EBP1(1:3000, Cell signaling, #9451), anti-eIF4E (1:3000, Cell signaling, #9742), anti-p-eIF4E (1:3000, Cell signaling, #9741), SP-1 (1:3000, Millipore, 07-645) Egr-1 (1:5000, Santa cruz sc-110), anti-flag (1:5000, Sigma), and anti-Gia1/2/3 (Santa Cruz. sc-26761, 1:3000). Each protein was quantified as a band using Immobilon™ Western Blotting Detection reagents (Millipore). The amounts of proteins used in each sample were found to be the same as measured by blotting with an anti-beta-actin antibody (1:10000, Cell signaling). In the case of the hstm1 protein, a serum obtained after the injection of peptides of SEQ ID NOS: 6 and 7 was purified using protein A agarose (5000:1).

Example 8

Measurement of cAMP in NIH3T3 Cells Transfected Transiently or Permanently with the Novel GPCR Gene To examine the function of hstm1, cAMP was quantified in the cell lines which transiently or stably expressed hstm1. All experiments were carried out along with NIH3T3 cells anchoring a mock vector. Cells were treated with forskolin (Sigma F3917), a cAMP inducer. Results furnished by experiments performed in triplicate showed that cAMP levels in the cells permanently expressing hstm1 were suppressed by 30% or more and that when stimulated with foskolin, the cAMP levels in the cells were lower by 40% or more than those in the cells anchoring a mock vector.

Figure 5:
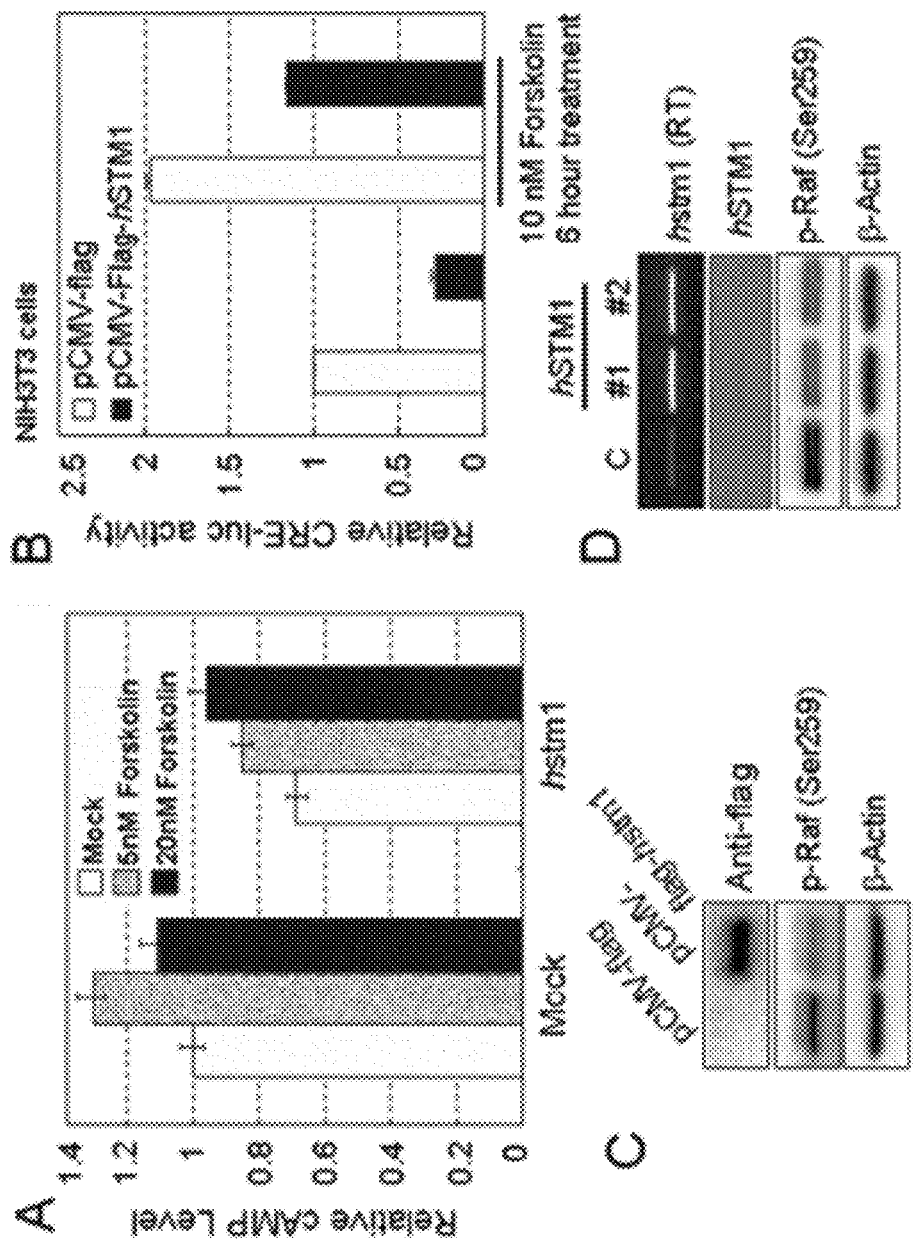
FIG. 5A shows changes in the cAMP level of normal cells overexpressing the GPCR gene (hstm1 gene) according to the concentration of forskolin, a cAMP activator.
FIG. 5B is a graph showing relative CRE (cAMP response element)-Luc reporter assay result in cells with or without overexpressing the GPCR gene (hstm1 gene) in the presence or absence of forskolin.
FIG. 5C shows the phosphorylation of p-raf1 gene in normal cells transiently overexpressing the GPCR gene (hstm1 gene).
FIG. 5D shows the phosphorylation of p-raf1 in normal cells stably overexpressing the GPCR gene (hstm1 gene).

FIG. 5A is a depiction of the cAMP levels in cells transfected permanently with hstm1 relative to those in wild-type NIH3T3.

In the case of transient transfection, the cAMP level was decreased by as much as 70% in the absence of forkolin stimulus, and thus the inhibitory effect was more significant. Upon forskolin stimulation, cAMP levels were suppressed by about 40% (FIG. 5B).

cAMP Assay

NIH3T3-IRES-EV and NIH3T3-IRES-hSTM1 stable cell lines were used to examine the effect of the hSTM1 gene on intracellular cAMP level, with the aid of cAMP-Glo™ assay kit (Promega).

First, NIH3T3-IRES-EV and NIH3T3-IRES-hSTM1a-A cells were plated at a density of 5000 cells per well into 96-well plates and grown to 80% confluence. Thereafter, the cells were washed with PBS and 20 μl of induction buffer with or without the addition of 20 μM forskolin to each well according to the manual of Promega. After incubation for 6 hours, 20 μl of cAMP-Glo™ lysis buffer was added to each well to lyze the cells which were then transferred to new 96-well plates (opaque white) for luciferase assay. To quantify cAMP, 40 μl of cAMP-Glo™ detection solution was added to each well and the plates were shaken for 1 min to promote the reaction and incubated at room temperature for 20 min, after which 80 μl of Kinase-Glo reagent was added and shaken for 1 min before incubation at room temperature for 10 min, according to the manual. Absorbance was read on a 96-well microplate reader. Values in the graph are relative to the unit (1) which is set for the cAMP level in NIH3T3-IRES-EV cells and were determined by computing the average of measurement results from independent experiments conducted in triplicate.

As for the transiently transfected NIH3T3 cells, they were subjected to the transfection process illustrated in Example 5 and the subsequent procedure was conducted in the same manner as described above.

Luciferase Reporter Assay

Using CRE-luc Reporter DNA plasmid, the effect of hSTM1 on cAMP level was examined. First, NIH3T3 mouse fibroblast was aliquoted at a density of $4\times10^4$ into 24-well plates and grown to 50% confluence in 10% FBS-DMEM. Together with 200 ng of reporter plasmid, 10 ng of Renilla (control for transfection efficiency) expression vector, 150-300 ng of pCMV-hSTM1 expression vector, and the control pCMV-taq1 expression vector were mixed to give a DNA mixture of 500 ng in total. To each DNA mixture was added 1 μl of Lipofectamine plus reagent (Invitrogen) in accordance with the manual of the manufacturer, followed by incubation for 15 min to form DNA complexes. During this, the cells were washed with PBS and suspended in serum-free medium. The DNA complex was aliquoted in a predetermined amount to each well and incubated for 4 hours. The cells were washed again with PBS and maintained in 10% FBS-supplemented medium. After incubation with the DNA complex for 48 hours, 100 μl of cell lysis buffer (for luciferase assay, Promega) was added to each well to prepare samples. Fifty pl of each sample was reacted with 50 μl of luciferin to measure the activity of the reporter with a luminometer. Then, stop buffer was added to measure the activity of Renilla with a luminometer. The value of reporter activity was divided by the renilla activity for each sample and was expressed on a relative scale related to the activity of test groups (samples with pCMV-hSTM1) to the control (samples with pCMV-taq1). Values in the figure were averages of the measurements obtained from four independent experiments.

In addition, a change in cAMP level is known to cause a change in the activity of the downstream effector Protein kinase A, which in turn affects the phosphorylation of raf1 kinase, an upstream factor of MAP kinase. As for hstm1 (permanent and transient), its effect on the phosphorylation of raf1 kinase, which leads to promoting cell growth, was examined using the Western blotting of p-raf1. Western blotting was performed in the same manner as in Example 6, with the exception that anti-p-raf (S259) was used (1:1000, Cell signaling #9421).

Example 9

Figure 6:
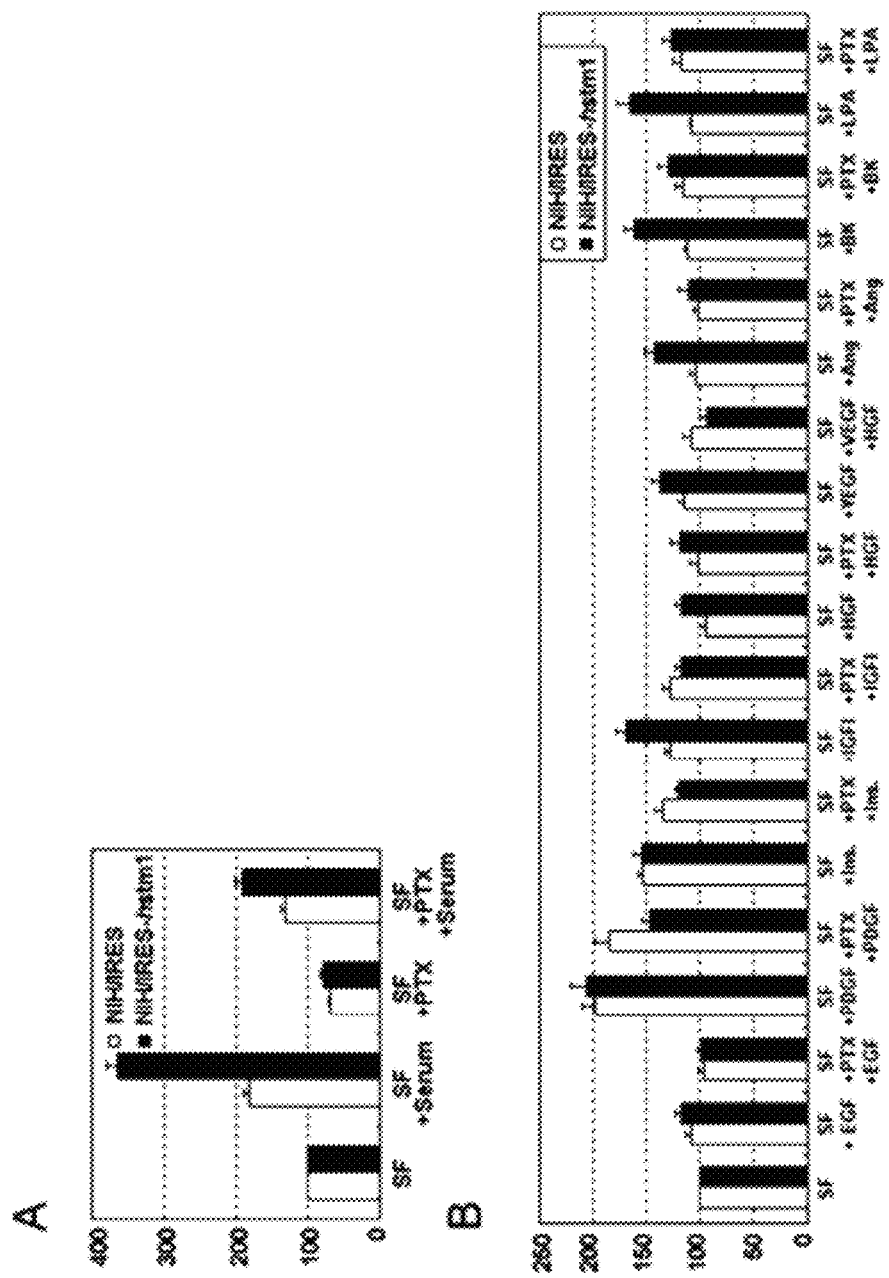
FIG. 6A shows the serum responses of normal cells stably overexpressing the GPCR gene (hstm1 gene) when they are treated with and without PTX.
FIG. 6B shows the responses of normal cells overexpressing the GPCR gene (hstm1 gene) to various growth factors and known GPCR ligands in the presence or absence of PTX.

Effect of External Upstream Signaling Transmitter on Cell Growth Promotion of the Novel GPCR External stimulation factors affecting the activity of hstm1 were investigated. In this regard, to examine the effects of cell growth factors and several known GPCR ligands on the cell growth promotion of hstm1, the extent of cell growth was analyzed using a WST assay (see Example 6). The G-protein which causing a decrease in cAMP level belongs to the G1 family and the signaling pathway mediated by the G-protein is known to be inhibited by PTX (Pertussis toxin). Therefore, a growth factor whose level varies depending on PTX may be highly likely to be a signaling factor upstream of hstm1. In this example, the addition of serum promoted cell growth by four fold, compared to the control, but its effect was decreased by treatment with PTX. Therefore, a signaling pathway which is inhibited by PTX is involved in the cell growth promotion of hstm1 (FIG. 6A).

In detail, growth factors and ligands in serum, such as EGF, PDGF, insulin, IGF-I, HGF, VEGF, angiotensin, bradkynin, and LPA, were examined for their ability to promote cell growth. Cell growth factors and their concentrations are summarized in Table, below. Treatment with PDGF, insulin, IGF-I, VEGF, angiotensin, Bradkynin, and LPA promoted cell growth while PTX inhibited the promotion. Thus, the cell growth factors and ligands are regarded as affecting the cell growth promotion of hstm1 (FIG. 6B).

TABLE 2

| Growth Factor | Company | Cat # | Final Conc. |
|---|---|---|---|
| EGF | R&D system | 236-EG | 200 ng/ml |
| PDGF | Calbiochem | 521225 | 20 ng/ml |
| Insulin | Sigma | I9278 | 1 µg/ml |
| IGF-1 | R&D system | 291-G1 | 0.2 ng/ml |
| HGF | R&D system | 294-HG | 20 ng/ml |
| VEGF | R&D system | 293-VE | 10 ng/ml |
| Angiotensin II | Sigma | A9525 | 200 nM |
| Bradykinin | Sigma | B3259 | 10 nM |
| LPA | Sigma | L7260 | 1 µM |

Example 10

Gene Expression Analysis Through RT-PCR

To examine a change in the expression of genes involved in the promotion of cell growth in each stable cell line, relative RNA levels of the cell growth factors IGF-I and II, and cyclin D1, illustrated in Example 1, were measured using RT-PCR. RNA isolation and cDNA synthesis were accomplished in the same manners as in Examples 3 and 4. PCR was performed using a Dr. Taq Master mix (Doctor Protein) according to the manual of the manufacturer. 2 µl of a 20 pmol stock for each primer was used. PCR primers sequences and annealing temperatures for each gene are summarized in Table 3, below.

As can be seen in FIG. 7A, the transcription of IGF-I, IGF-II, and cyclin D1 was promoted in the hstm1-overexpressing cells.

Example 11

Immunoneutralization Assay for Effect of IGF-I and IGF-II on Cell Growth

The overexpression of IGF-I and IGF-II in hstm-expressing cells was revealed in Example 9. Thus, an experiment was carried out to examine whether the cell growth promotion of hstm1-expressing cells was decreased or not when IGF-1 and IGF-II were prevented from binding to the receptor by neutralization with antibodies. In this regard, cell cultures were treated with 40 µg/ml of anti-IGF-I and anti-IGF-II antibodies to halt the function of IGF-I or IGF-II present in the medium and cell growth was analyzed with an SRB assay. Changes in protein expression were examined by subjecting proteins isolated from the same samples to Western blotting. As a result, neutralization with the anti-IGF-1 antibody revealed a decrease in the cell growth of the control by 12% and the experimental groups by 25% (FIGS. 7C and 7D) while no significant changes in the expression level of p-Erk1/2, cyclin D1 and p-AKT were detected with a Western blot (FIG. 7 B). In the presence of the anti-IGF-II antibody, the cell growth of the control and the test group was decreased by 18% and 35%, respectively (FIGS. 7C and D), and western blots indicated a change in the expression level of p-erk1/2, cyclin D1 and p-AKT (FIG. 7B). When treated with both antibodies to IGF-I and IGF-II, the cells were observed to grow at slower rates, but there were no differences in the protein expression pattern from an antibody to IGF-II alone on Western blots. Therefore, IGF-I and IGF-II (especially IGF-II) were implicated in hstm1-induced cell growth promotion.

Immunoneutralization Assay

NIH3T3/IRES-EV and NIH3T3/IRES-hSTM1 cell lines were seeded at a density of $1 \times 10^5$ cells per well into 12-well plates and at a density of 5,000 cells per well into 96-well plates and grown to 50% confluence. Thereafter, the medium

TABLE 3

| | | Primer Sequence | Annealing Temp.(° C.) | Cycle |
|---|---|---|---|---|
| GAPDH F | SEQ ID NO: 10 | 5'-CTACATGGTCTACATGTTCC-3' | 55 | 25 |
| GAPDH R | SEQ ID NO: 11 | 5'-CTGACAATCTTGAGTGAGTT-3' | | |
| IGF-1 F | SEQ ID NO: 12 | 5'-CCTCTTCTACCTGGCGCTCT-3' | 62 | 42 |
| IGF-1 R | SEQ ID NO: 13 | 5'-GGGACTTCTGAGTCTTGGGC-3' | | |
| IGF-2 F | SEQ ID NO: 14 | 5'-GGACCGCGGCTTCTACTTCAG-3' | 58.7 | 37 |
| IGF-2 R | SEQ ID N0: 15 | 5'-GACCCCGGCGGGCACGCAGGA-3' | | |
| cyclin D1 F | SEQ ID N0: 16 | 5'-GAACACTTCCTCTCCAAAATG-3' | 58.7 | 40 |
| cyclin D1 R | SEQ ID NO: 17 | 5'-GTTCTGCTGGGCCTGGCGCAG-3' | | |
| hSTM1a F | SEQ ID NO: 18 | 5'-TCATCAAAGCCTACAAGACGG-3' | 57 | 40 |
| hSTM1a R | SEQ ID NO: 19 | 5'-GGTGGACTTCCGGAGGAAGTT-3' | | | was replaced with 5% FBS-DMEM containing PBS for a control and with 5% FBS-DMEM containing anti-IGF-1 antibody (Santacuz, 40 μg/ml), anti-IGF-2 antibody (Santacuz, 40 μg/ml) or both of the antibodies (40 μg/ml) for the test group. After the incubation of the cell lines with the antibodies for 24 hours, the cells in the 12-well plates were washed once with PBS, and proteins were isolated with RIPA cell lysis buffer and used for Western blotting with anti-Cyclin D1 antibody, anti-phospho-ERK1/2 antibody, anti-ERK1/2 antibody, and anti-p-AKT antibody. The cells in the 96-well plates were fixed with one volume of a 10% formalin solution. After incubation for 20 min, the cells were washed with PBS and dried overnight. To the dried cells was added 1% SRB, followed by incubation for one hour to stain the cells. The staining solution was discarded and the cells were washed again with distilled water and dried. The dye was extracted by adding 10 mM Tris to the dried cells and transferred to new 96-well plates, followed by measuring absorbance at 540 nm. The absorbance was used to analyze the effects of the immunoneutralization on cell proliferation.

Example 12

Identification of G-Protein Coupled with the Novel GPCR

1) In Vitro Binding—Identification of Associated G-Protein with His Tagged Hstm1
a. Preparation of 6×His Tagged Protein
hSTM1 was inserted into the *E. coli* expression vector pET28a for use in 4×His tagging. *E. coli* BL21 was transformed with pET28a or pET28a-hSTM1. When the cells were grown to $OD_{600}$=0.5, IPTG was added at a final concentration of 0.5 mM to induce the expression of the protein during incubation at 20° C. for 8 hours with shaking.

The cells were harvested by centrifugation, suspended in IX-binding buffer (20 mM Tris, 500 mM NaCl, pH 7.5+ Protease inhibitors) and ruptured using a sonicator. After centrifugation (12,000 rpm, 30 min, 4° C.), the supernatant was allowed to pass through a syringe filter (0.45 μm).
b. Binding of 6× His Tagged Protein to His-Binding Agarose Resin
  1. Ni-charged His-binding agarose resin, purchased from ELPIS (ELPIS Cat. No. EBE-1031), was washed with three volumes of distilled water and then with three volumes of 1× binding buffer.
  2. The resin of 1 was added to each of the 6×His-tagged protein samples of step a, and spun at 4° C. for 3 hours to allow the protein to bind to the His resin.
  3. The samples of 2 were loaded to columns and washed three times with 0.6-0.7 volumes of binding buffer.
c. Preparation of Total Cell Lysate to be Reacted with the 6×His-Tagged Protein Bound to the His-Binding Agarose Resin The SW620 cell line was cultured on a large scale, harvested with D-PBS (Dulbecco's Phosphate-Buffered Saline, GIBCO, Ca. No. 21600-010), and ruptured using a sonicator. After the centrifugation of the ruptured cells (12,000 rpm, 30 min, 4° C.), the supernatant was allowed to pass through a syringe filter (0.45 μm). H is resin was added to the filtered, total cell lysate and spun at 4° C. for 3 hours to remove unnecessary proteins.
  d. Detection of Proteins Interacting with 6× Hiss-Tagged Proteins Bound to His-Binding Agarose Resin The cell lysate of step c was added to the resin of step b to which the His-tagged protein was bound, mixed at 4° C. for 12 hours, and washed three times with D-PBS. The proteins of the cell lysate, bound to the His-tagged protein, were eluted by adding various concentrations of NaCl buffer, and the eluates were combined with SDS sample buffer and denatured at 95° C. for 15 min, followed by electrophoresis on 10% SDS-PAGE gel. The proteins were identified by Western blotting with antibodies including anti-His, and anti-Gαi1/2/3. Western blotting patterns showed that a Gαi subunit is coupled with hstm1.
  2) Immunoprecipitation—Identification of Coupled, G-Protein Using Flag-Tagged Hstm1

SW620 cells were transfected with Flag-tagged hstm1, incubated for 72 hours and used to prepare samples in the same manner as in Example 11. After the Flag-tagged hstm1 was bound to Flag beads (Sigma), other proteins were removed in the same manner as in step d. Proteins coupled with the receptor were identified using electrophoresis and Western blotting with antibodies such as anti-flag and anti-Gαi1/2/3. Information on the antibodies is illustrated in Example 6.

Example 13

Examination of Signal Transduction Pathway with siRNA

1) Inhibition of G-Protein siRNA Against hstm1-Mediated Signal Transduction and Determination of Related God Subunit Gene knockdown with siRNA was performed to examine which isotype of the Gαi protein relays hSTM1a-mediated signal transduction. NIH3T3-IRES-EV and NIH3T3-IRES-hSTM1 cell lines were seeded at a density of $1.5 \times 10^3$ and $2 \times 10^5$ cells per well into 6-well plates and grown to 40% confluence. Separately, 5 μl of each of siRNA and scramble siRNA (1+2) (stock: 20 nmol) for Gαi-1, Gαi-2 and Gαi-3 was added to 500 μl of serum-free DMEM. To each of these samples was added 15 μl of Hiperfect (Qiagen), a transfection reagent using siRNA, according to the manual of the manufacturer, and they were thoroughly mixed using a stirrer and left at room temperature for 15 min to form siRNA transfection complexes. During the formation, the medium in each well was replaced with 1.5 ml of fresh 10% FBS-DMEM. After a period of 15 min had passed, each sample was dropwise added to each well (siRNA added at a final concentration of 5 pmol to cells). After incubation for 48 hours, the transfection procedure using Hiperfect (Qiagen) was repeated again with the same concentration of siRNA. Twenty four hours after the second addition of siRNA, 200 μl of RIPA cell lysis buffer or 500 μl of Trizol was added to each well to extract protein or RNA from the cells.

Only 30 μg of each protein extract was used in SDS-PAGE and Western blotting to determine which protein had its expression level changed by the gene knockdown of Gαi-1, Gαi-2 and Gαi-3 using siRNA.

As for the RNA extract, it was applied to RT-PCR to examine which gene was changed in mRNA expression level by the gene knockdown using siRNA. The nucleotide sequences of the siRNA and RT-PCR primers used are summarized in Table 4, below.

TABLE 4

| siRNA Name | | 5'-Sequence-3' |
|---|---|---|
| scrambled 1 | SEQ ID NO: 20 | GUCCACAUUCGACGCCCAC |
| | SEQ ID NO: 21 | GUGGGCGUCGAAUGUGGAC |

TABLE 4-continued

| siRNA Name | | 5'-Sequence-3' |
|---|---|---|
| scrambled 2 | SEQ ID NO: 22 | AGCGCUGACAACAGUUUCA |
| | SEQ ID NO: 23 | UGAAACUGUUGUCAGCGCU |
| Gαi-1 | SEQ ID NO: 24 | GCACAGAGUGACUACAUCC |
| | SEQ ID NO: 25 | GGAUGUAGUCACUCUGUGC |
| Gαi-2 | SEQ ID NO: 26 | GGAGUGCUGAAGAAGGAGU |
| | SEQ ID NO: 27 | ACUCCUUCUUCAGCACUCC |
| Gαi-3 | SEQ ID NO: 28 | AGCUGCUUACAUUCAGUGC |
| | SEQ ID NO: 29 | GCACUGAAUGUAAGCAGCU |

TABLE 5

| | | Primer Sequence | Annealing Temp.(° C.) | Cycle |
|---|---|---|---|---|
| GAPDH F | SEQ ID NO: 10 | 5'-CTACATGGTCTACATGTTCC | 55 | 25 |
| GAPDH R | SEQ ID NO: 11 | 5'-CTGACAATCTTGAGTGAGTT | | |
| IGF-1 F | SEQ ID NO: 12 | 5'-CCTCTTCTACCTGGCGCTCT | 62 | 42 |
| IGF-1 R | SEQ ID NO: 13 | 5'-GGGACTTCTGAGTCTTGGGC | | |
| IGF-2 F | SEQ ID NO: 14 | 5'-GGACCGCGGCTTCTACTTCAG | 58.7 | 37 |
| IGF-2 R | SEQ ID NO: 15 | 5'-GACCCCGGCGGGCACGCAGGA | | |
| Gαi-1 F | SEQ ID NO: 30 | 5'-GGCGGATGATGCTCGCCAACT | 60.6 | 42 |
| Gαi-1 R | SEQ ID NO: 31 | 5'-GATGACGTCTGTTACAGCATC | | |
| Gαi-2 F | SEQ ID NO: 32 | 5'-GTGACTACATCCCTACACAGC | 57 | 40 |
| Gαi-2 R | SEQ ID NO: 33 | 5'-GACGGCATCGAACACAAACTG | | |
| Gαi-3 F | SEQ ID NO: 34 | 5'-GAACCGAATGCATGAAAGCAT | 57 | 35 |
| Gαi-3 R | SEQ ID NO: 35 | 5'-TGATGACATCCGTAACAGCAT | | |

The same samples were subjected to Western blotting against cyclinD1 and β-actin to monitor the expression levels of the proteins, indicating that the hstm1-mediated signal transduction was inhibited by Gαi-2 and Gαi-3 siRNAs.

2) Inhibition of hstm1 siRNA Against Growth Potential of Cancer Cell Lines

After being treated for 48 hours with hstm1 siRNA in the same manner as in 1), the cell growth of stomach cancer cells and liver cancer cells was monitored. FIGS. 9A and 9B show stomach cancer cells and liver cancer cells, respectively, on plates after treatment with hstm1 siRNA (si-hstm1). When treated with si-hstm1, the cells grew at slower rates as can be seen in terms of cell morphology and saturation. Quantitative analysis results obtained by WST assay are graphically provided (FIG. 9C). Although some cell lines gave no responses, the quantitative graph shows the inhibition of si-hstm1 against most cancer cell lines (5/7) and liver cancer cell lines (2/4). The sequences of siRNA used are given in Table 6 and the sequences of predicted hstm1 siRNA are summarized in Table 7, below.

TABLE 6

| siRNA Name | | 5'-Sequence-3' |
|---|---|---|
| scrambled-1 | SEQ ID NO: 20 | GUCCACAUUCGACGCCCAC |
| | SEQ ID NO: 21 | GUGGGCGUCGAAUGUGGAC |
| scrambled 2 | SEQ ID NO: 22 | AGCGCUGACAACAGUUUCA |
| | SEQ ID NO: 23 | UGAAACUGUUGUCAGCGCU |

TABLE 6-continued

| siRNA Name | | 5'-Sequence-3' |
|---|---|---|
| hstm1-1 | SEQ ID NO: 36 | CCGUGCUGUUGUUCCUCAU |
| | SEQ ID NO: 37 | AUGAGGAACAACAGCACGG |
| hstm1-2 | SEQ ID NO: 38 | UCCAGCGUGUUGUACCUGC |
| | SEQ ID NO: 39 | GCAGGUACAACACGCUGGA |

TABLE 7

| siRNA Name | | 5'-Sequence-3' |
|---|---|---|
| 1361/2279 | SEQ ID NO: 40 | GGGGAUCUCCUACUCUCUG |
| | SEQ ID NO: 41 | CAGAGAGUAGGAGAUCCCC |
| 1509/2279 | SEQ ID NO: 42 | CUGCUGCUCGACACCAUCA |
| | SEQ ID NO: 43 | UGAUGGUGUCGAGCAGCAG |
| 1322/2279 | SEQ ID NO: 44 | GCCUCAGAUCCGCACCAAC |
| | SEQ ID NO: 45 | GUUGGUGCGGAUCUGAGGC |
| 1511/2279 | SEQ ID NO: 46 | GCUGCUCGACACCAUCAUC |
| | SEQ ID NO: 47 | GAUGAUGGUGUCGAGCAGC |
| 1015/2279 | SEQ ID NO: 48 | AGACCUACACGGCUGUGUA |
| | SEQ ID NO: 49 | UACACAGCCGUGUAGGUCU |
| 1052/2279 | SEQ ID NO: 50 | GGUGAUGCUGACGCUGUAC |
| | SEQ ID NO: 51 | GUACAGCGUCAGCAUCACC |

Example 14

Migration and Invasion Assay

To examine the motility of hstm1-overexpressing cell lines, isolated cells were placed on an ibidi Culture-Insert (Cat No. 80206) in a dish and allowed to adhere to the bottom of the insert. The culture-insert was removed to monitor the migration of the cells through the path constructed within the insert. They were observed and photographed under a microscope according to time.

As can be seen in the photographs, a greater number of hstm1-expressing cell lines moved through intercellular spaces, compared to the control, indicating that the hstm1-overexpressing cell lines are of higher motility (FIG. 10A).

Also, the metastatic ability of hstm1-overexpressing cells was examined using the ECM invasion chamber (70019) of Chemicon. A serum-free medium was incubated for 30 min within the chamber so that it was rendered to be suitable for use in invasion assay. The cells resuspended in serum-free medium were counted and put inside the chamber while a medium supplemented with 10% serum was placed in outside wells of the chamber, followed by incubation for 24 hours in a $CO_2$ incubator. Thereafter, the chamber was removed, and the cells were stained with a 1% crystal violet solution. Excessive dye was washed off with water, after which the cells which invaded from the inside of the chamber to the outside were observed (FIG. 10B). From the stained cells, the dye was separated into 1% acetic acid, and used to read absorbance on a spectrophotometer. As can be seen, hstm1-overexpressing cell lines were increased in metastatic ability (FIG. 10B).

The invention claimed is:

1. A method for the treatment of stomach cancer, comprising administering to a subject in need thereof an agent inhibiting the expression of a polynucleotide encoding a GPCR polypeptide having the amino acid sequence of SEQ ID NO: 1, wherein the stomach cancer over-expresses the GPCR polypeptide having the amino acid sequence of SEQ ID NO: 1.

2. The method of claim 1, wherein the agent inhibiting the expression of the polynucleotide is an antisense oligonucleotide, siRNA or shRNA against the polynucleotide encoding a GPCR polypeptide having the amino acid sequence of SEQ ID NO: 1.

3. The method of claim 2, wherein the siRNA has a nucleotide sequence selected from the group consisting of SEQ ID NOS: 20 to 23, SEQ ID NOS: 36 to 51, and a combination thereof.

4. The method of claim 1, wherein the stomach cancer is metastatic cancer.

* * * * *

```
                            SEQUENCE LISTING

<160> NUMBER OF SEQ ID NOS: 51

<210> SEQ ID NO 1
<211> LENGTH: 291
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: hstm1 isoform 1

<400> SEQUENCE: 1

Met Val Trp Lys Lys Leu Gly Ser Arg Asn Phe Ser Ser Cys Pro Ser
 1               5                  10                  15

Gly Ser Ile Gln Trp Ile Trp Asp Val Leu Gly Glu Cys Ala Gln Asp
            20                  25                  30

Gly Trp Asp Glu Ala Ser Val Gly Leu Gly Leu Ile Ser Ile Leu Cys
        35                  40                  45

Phe Ala Ala Ser Thr Phe Pro Gln Phe Ile Lys Ala Tyr Lys Thr Gly
    50                  55                  60

Asn Met Asp Gln Ala Leu Ser Leu Trp Phe Leu Leu Gly Trp Ile Gly
65                  70                  75                  80

Gly Asp Ser Cys Asn Leu Ile Gly Ser Phe Leu Ala Asp Gln Leu Pro
                85                  90                  95

Leu Gln Thr Tyr Thr Ala Val Tyr Tyr Val Leu Ala Asp Leu Val Met
            100                 105                 110

Leu Thr Leu Tyr Phe Tyr Tyr Lys Phe Arg Thr Arg Pro Ser Leu Leu
        115                 120                 125

Ser Ala Pro Ile Asn Ser Val Leu Leu Phe Leu Met Gly Met Ala Cys
    130                 135                 140

Ala Thr Pro Leu Leu Ser Ala Ala Gly Pro Val Ala Ala Pro Arg Glu
145                 150                 155                 160

Ala Phe Arg Gly Arg Ala Leu Leu Ser Val Glu Ser Gly Ser Lys Pro
                165                 170                 175

Phe Thr Arg Gln Glu Val Ile Gly Phe Val Ile Gly Ser Ile Ser Ser
            180                 185                 190

Val Leu Tyr Leu Leu Ser Arg Leu Pro Gln Ile Arg Thr Asn Phe Leu
        195                 200                 205

Arg Lys Ser Thr Gln Gly Ile Ser Tyr Ser Leu Phe Ala Leu Val Met
    210                 215                 220

Leu Gly Asn Thr Leu Tyr Gly Leu Ser Val Leu Leu Lys Asn Pro Glu
225                 230                 235                 240

Glu Gly Gln Ser Glu Gly Ser Tyr Leu Leu His His Leu Pro Trp Leu
                245                 250                 255

Val Gly Ser Leu Gly Val Leu Leu Asp Thr Ile Ile Ser Ile Gln
            260                 265                 270

Phe Leu Val Tyr Arg Arg Ser Thr Ala Ala Ser Glu Leu Glu Pro Leu
```

```
            275                 280                 285

Leu Pro Ser
    290

<210> SEQ ID NO 2
<211> LENGTH: 226
<212> TYPE: PRT
<213> ORGANISM: Homo sapiens
<220> FEATURE:
<221> NAME/KEY: PEPTIDE
<222> LOCATION: (1)..(226)
<223> OTHER INFORMATION: hstm1 isoform 2

<400> SEQUENCE: 2

Met Asp Gln Ala Leu Ser Leu Trp Phe Leu Leu Gly Trp Ile Gly Gly
  1               5                  10                  15

Asp Ser Cys Asn Leu Ile Gly Ser Phe Leu Ala Asp Gln Leu Pro Leu
                 20                  25                  30

Gln Thr Tyr Thr Ala Val Tyr Tyr Val Leu Ala Asp Leu Val Met Leu
             35                  40                  45

Thr Leu Tyr Phe Tyr Tyr Lys Phe Arg Thr Arg Pro Ser Leu Leu Ser
 50                  55                  60

Ala Pro Ile Asn Ser Val Leu Leu Phe Leu Met Gly Met Ala Cys Ala
 65                  70                  75                  80

Thr Pro Leu Leu Ser Ala Ala Gly Pro Val Ala Ala Pro Arg Glu Ala
                 85                  90                  95

Phe Arg Gly Arg Ala Leu Leu Ser Val Glu Ser Gly Ser Lys Pro Phe
            100                 105                 110

Thr Arg Gln Glu Val Ile Gly Phe Val Ile Gly Ser Ile Ser Ser Val
        115                 120                 125

Leu Tyr Leu Leu Ser Arg Leu Pro Gln Ile Arg Thr Asn Phe Leu Arg
130                 135                 140

Lys Ser Thr Gln Gly Ile Ser Tyr Ser Leu Phe Ala Leu Val Met Leu
145                 150                 155                 160

Gly Asn Thr Leu Tyr Gly Leu Ser Val Leu Leu Lys Asn Pro Glu Glu
                165                 170                 175

Gly Gln Ser Glu Gly Ser Tyr Leu Leu His His Leu Pro Trp Leu Val
            180                 185                 190

Gly Ser Leu Gly Val Leu Leu Asp Thr Ile Ile Ser Ile Gln Phe
        195                 200                 205

Leu Val Tyr Arg Arg Ser Thr Ala Ala Ser Glu Leu Glu Pro Leu Leu
210                 215                 220

Pro Ser
225

<210> SEQ ID NO 3
<211> LENGTH: 2254
<212> TYPE: DNA
<213> ORGANISM: Homo sapiens
<220> FEATURE:
<221> NAME/KEY: gene
<222> LOCATION: (1)..(2254)
<223> OTHER INFORMATION: hstm1 isoform 1 (variant 1)

<400> SEQUENCE: 3
agcgcgcggc gtgggggcgg ggcctgcggt tcccgcgggg gcggtggcgc gcggtcagct     60
gacccggcgg gccttgaccc agaagctggg ccctggcggc ggatctggac gtggtgagcc    120
ggaccggggg caggtggcaa acttcacggc tggggtcgg ggctcctggg cttccctgcc    180
```

-continued

```
acatccttcc agccctctcc tccggccgct ggactgtccc ggctcctgcg ccctccttgt    240
ggcgcgatat cgtgggacga ggctccgggc cgggactggg tggccctcgg gaatccgcag    300
ccagtggccc cccacctcaa aggcgaccag cgcggcctct cgagctggcc tggccaggag    360
ttgccctgcc ccggccgacc ggccccttgg catctgatgg cttcgttttt cccgggccgg    420
ccgggcgagg ggccctcgcg gcgctggccc cagcagctgt cctatcatta tccctccaaa    480
caggcggccc gcgccgggct gagtcaccag gagggagctg tggccgagga cgccgaggcc    540
tggagtgggt ggtagccccg agctgggacg ctcctccctc cacaatctcc ccaggtctgc    600
agggaccgag ggcctacact gcctcctccc acgccgtgct taggaaccct tgctggcctc    660
agaacaccag cgccctccct ccggtgcagc cctgcctggc cggggccccc tcctccacag    720
ccatggtctg gaagaaactg ggctcccgca acttctccag ctgccccagt ggctccatcc    780
agtggatatg ggatgtgttg ggtgaatgtg cccaggacgg ctgggacgag ccagcgtgg    840 gcctgggctt gatctccatt ctctgctttg ctgcatctac cttcccccag ttcatcaaag    900
cctacaagac gggcaacatg gaccaggcgc tgtccctgtg gttcctcctg ggctggattg    960
gcggagactc ctgcaacctc atcggctcct tccttgctga ccagctgccc ctgcagacct   1020
acacggctgt gtattatgtc ttggcagacc tggtgatgct gacgctgtac ttttactaca   1080
agttcaggac gcgcccctct ctgttgtctg ccccatcaa ctccgtgctg ttgttcctca   1140
tggggatggc gtgcgccaca ccgctgctga gtgctgctgg gcccgtggct gcccctaggg   1200
aagccttccg ggggcgggcg ctcctgtccg tggagtcggg cagcaagccc ttcacccggc   1260
aggaagtcat tggcttcgtc atcggctcca tctccagcgt gttgtacctg ctttcccggc   1320
tgcctcagat ccgcaccaac ttcctccgga agtccaccca ggggatctcc tactctctgt   1380
tcgcgctggt gatgctgggg aacacgctgt atgggctgag cgtgctgctc aaaaaccccg   1440
aggagggcca gagcgagggc agctaccgtgc tgcaccacct gccctggctt gtgggcagcc   1500
tgggcgtgct gctgctcgac accatcatct ccatccagtt cctggtgtac aggcgcagca   1560
ccgccgcctc ggagcttgag cccctcctcc ccagctgacc agaaccaggc tgagcgcagg   1620
aggacaggca ccaccggatg ccacaccagg caggaggagg tgtggacagt gatggtacgg   1680
cggccctgca tcagcctgcg ggtggcctct ggatcctccg tggaccgaac cgtcccccca   1740
ggaacacacc ttcaggtaga ccccgaagcc tcaaggccgg ggctggagcg agacccccag   1800
ggcctctcag gagacagtga ggctgcccct cctaccacct acctcattct gcctactcac   1860
cccaggggca cagccacag cctgctggac tcaggactgt cctgtcaact ccagacaact   1920
gaataaacag gccgggtaca gtggctcgca cctgtaatcc tagcactttg ggaggccgaa   1980
gcgggtggac cacttgacgt ccgtagttcg agaccagcct ggccaacatg gtgaaacccc   2040
atctctacta aaaatacaaa aattagccag gtgtggtggc acacatctgt agtcccagct   2100
acttgggagg ctgaggcagg agaactgttt gaacctggga cagaggtt gcggtgaacc   2160 gagatcgtgc cactgtactc cagcctgggt gacagagtga gactccgtct caaaaaaata   2220
aaaaagataa ccgaggaaac ggtacctccc catg                              2254
```

<210> SEQ ID NO 4
<211> LENGTH: 1884
<212> TYPE: DNA
<213> ORGANISM: Homo sapiens
<220> FEATURE:
<221> NAME/KEY: gene
<222> LOCATION: (1)..(1884)

<223> OTHER INFORMATION: hstm1 isoform 1 (variant 2)

<400> SEQUENCE: 4

| | | | | | |
|---|---|---|---|---|---|
| agcgcgcggc | gtgggggcgg | ggcctgcggt | tcccgcgggg | gcggtggcgc | gcggtcagct | 60 |
| gacccggcgg | gccttgaccc | agaagctggg | ccctggcggc | ggatctggac | gtggcggccc | 120 |
| gcgccgggct | gagtcaccag | gagggagctg | tggccgagga | cgccgaggcc | tggagtgggt | 180 |
| ggtagccccg | agctgggacg | ctcctccctc | cacaatctcc | ccaggtctgc | agggaccgag | 240 |
| ggcctacact | gcctcctccc | acgccgtgct | taggaaccct | tgctggcctc | agaacaccag | 300 |
| cgccctccct | ccggtgcagc | cctgcctggc | cgggggcccc | tcctccacag | ccatggtctg | 360 |
| gaagaaactg | ggctcccgca | acttctccag | ctgccccagt | ggctccatcc | agtggatatg | 420 |
| ggatgtgttg | ggtgaatgtg | cccaggacgg | ctgggacgag | gccagcgtgg | gcctgggctt | 480 |
| gatctccatt | ctctgctttg | ctgcatctac | cttcccccag | ttcatcaaag | cctacaagac | 540 |
| gggcaacatg | gaccaggcgc | tgtccctgtg | gttcctcctg | ggctggattg | gcggagactc | 600 |
| ctgcaacctc | atcggctcct | tccttgctga | ccagctgccc | ctgcagacct | acacggctgt | 660 |
| gtattatgtc | ttggcagacc | tggtgatgct | gacgctgtac | ttttactaca | agttcaggac | 720 |
| gcgcccctct | ctgttgtctg | ccccatcaa | ctccgtgctg | ttgttcctca | tggggatggc | 780 |
| gtgcgccaca | ccgctgctga | gtgctgctgg | gcccgtggct | gcccctaggg | aagccttccg | 840 |
| ggggcgggcg | ctcctgtccg | tggagtcggg | cagcaagccc | ttcacccggc | aggaagtcat | 900 |
| tggcttcgtc | atcggctcca | tctccagcgt | gttgtacctg | ctttcccggc | tgcctcagat | 960 |
| ccgcaccaac | ttcctccgga | agtccaccca | ggggatctcc | tactctctgt | tcgcgctggt | 1020 |
| gatgctgggg | aacacgctgt | atgggctgag | cgtgctgctc | aaaaacccccg | aggagggcca | 1080 |
| gagcgagggc | agctacctgc | tgcaccacct | gccctggctt | gtgggcagcc | tgggcgtgct | 1140 |
| gctgctcgac | accatcatct | ccatccagtt | cctggtgtac | aggcgcagca | ccgccgcctc | 1200 |
| ggagcttgag | cccctcctcc | ccagctgacc | agaaccaggc | tgagcgcagg | aggacaggca | 1260 |
| ccaccggatg | ccacaccagg | caggaggagg | tgtggacagt | gatggtacgg | cggccctgca | 1320 |
| tcagcctgcg | ggtggcctct | ggatcctccg | tggaccgaac | cgtcccccca | ggaacacacc | 1380 |
| ttcaggtaga | ccccgaagcc | tcaaggccgg | ggctggagcg | gagacccccag | ggcctctcag | 1440 |
| gagacagtga | ggctgcccct | cctaccacct | acctcattct | gcctactcac | cccaggggcc | 1500 |
| acagccacag | cctgctggac | tcaggactgt | cctgtcaact | ccagacaact | gaataaacag | 1560 |
| gccgggtaca | gtggctcgca | cctgtaatcc | tagcactttg | ggaggccgaa | gcgggtggac | 1620 |
| cacttgacgt | ccgtagttcg | agaccagcct | ggccaacatg | gtgaaacccc | atctctacta | 1680 |
| aaaatacaaa | aattagccag | gtgtggtggc | acacatctgt | agtcccagct | acttgggagg | 1740 |
| ctgaggcagg | agaactgttt | gaacctggga | gacagaggtt | gcggtgaacc | gagatcgtgc | 1800 |
| cactgtactc | cagcctgggt | gacagagtga | gactccgtct | caaaaaaata | aaaagataa | 1860 |
| ccgaggaaac | ggtacctccc | catg | | | | 1884 |

<210> SEQ ID NO 5
<211> LENGTH: 1642
<212> TYPE: DNA
<213> ORGANISM: Homo sapiens
<220> FEATURE:
<221> NAME/KEY: gene
<222> LOCATION: (1)..(1642)
<223> OTHER INFORMATION: hstm1 isoform 2 (variant 3)

<400> SEQUENCE: 5

```
agcgcgcggc gtgggggcgg ggcctgcggt tcccgcgggg gcggtggcgc gcggtcagct    60
gacccggcgg gccttgaccc agaagctggg ccctggcggc ggatctggac gtggcggccc   120
gcgccgggct gagtcaccag gagggagctg tggccgagga cgccgaggcc tggagtgggt   180
ggtagcccg agctgggacg ctcctccctc cacaatctcc ccaggtctgc agggaccgag    240
ggcctacact gcctcctccc acgccgtgct taggccagtt catcaaagcc tacaagacgg   300
gcaacatgga ccaggcgctg tccctgtggt tcctcctggg ctggattggc ggagactcct   360
gcaacctcat cggctccttc cttgctgacc agctgccct gcagacctac acggctgtgt    420
attatgtctt ggcagacctg gtgatgctga cgctgtactt ttactacaag ttcaggacgc   480
gcccctctct gttgtctgcc ccatcaact ccgtgctgtt gttcctcatg gggatggcgt    540
gcgccacacc gctgctgagt gctgctgggc cgtggctgc ccctagggaa gccttccggg    600
ggcgggcgct cctgtccgtg gagtcgggca gcaagccctt cacccggcag gaagtcattg   660
gcttcgtcat cggctccatc tccagcgtgt tgtacctgc ttcccggctg cctcagatcc    720
gcaccaactt cctccggaag tccacccagg ggatctccta ctctctgttc gcgctggtga   780
tgctggggaa cacgctgtat gggctgagcg tgctgctcaa aaaccccgag gagggccaga   840
gcgagggcag ctacctgctg caccacctgc cctggcttgt gggcagcctg ggcgtgctgc   900
tgctcgacac catcatctcc atccagttcc tggtgtacag gcgcagcacc gccgcctcgg   960
agcttgagcc cctcctcccc agctgaccag aaccaggctg agcgcaggag acaggcacc   1020
accggatgcc acaccaggca ggaggagtg tggacagtga tggtacggcg gccctgcatc   1080
agcctgcggg tggcctctgg atcctccgtg gaccgaaccg tccccccagg aacacacctt   1140
caggtagacc ccgaagcctc aaggccgggg ctggagcgga cccccaggg cctctcagga   1200
gacagtgagg ctgcccctcc taccacctac ctcattctgc ctactcaccc cagggccac    1260
agccacagcc tgctggactc aggactgtcc tgtcaactcc agacaactga ataaacaggc   1320
cgggtacagt ggctcgcacc tgtaatccta gcactttggg aggccgaagc gggtggacca   1380
cttgacgtcc gtagttcgag accagcctgg ccaacatggt gaaacccat ctctactaaa    1440
aatacaaaaa ttagccaggt gtggtggcac acatctgtag tcccagctac ttgggaggct   1500
gaggcaggag aactgtttga acctgggaga cagaggttgc ggtgaaccga gatcgtgcca   1560
ctgtactcca gcctgggtga cagagtgaga ctccgtctca aaaaaataaa aaagataacc   1620
gaggaaacgg tacctcccca tg                                           1642
```

<210> SEQ ID NO 6
<211> LENGTH: 16
<212> TYPE: PRT
<213> ORGANISM: Artificial Sequence
<220> FEATURE:
<223> OTHER INFORMATION: sequence for producing hstm1 antibody
<220> FEATURE:
<221> NAME/KEY: PEPTIDE
<222> LOCATION: (2)..(16)
<223> OTHER INFORMATION: epitope of hstm1

<400> SEQUENCE: 6

Cys Lys Phe Arg Thr Arg Pro Ser Leu Leu Ser Ala Pro Ile Asn Ser
 1               5                  10                  15

<210> SEQ ID NO 7
<211> LENGTH: 17
<212> TYPE: PRT
<213> ORGANISM: Artificial Sequence

```
<220> FEATURE:
<223> OTHER INFORMATION: sequence for producing hstm1 antibody
<220> FEATURE:
<221> NAME/KEY: PEPTIDE
<222> LOCATION: (2)..(17)
<223> OTHER INFORMATION: epitope of hstm1

<400> SEQUENCE: 7

Cys Tyr Arg Arg Ser Thr Ala Ala Ser Glu Leu Glu Pro Leu Leu Pro
  1               5                  10                  15
Ser

<210> SEQ ID NO 8
<211> LENGTH: 20
<212> TYPE: DNA
<213> ORGANISM: Artificial Sequence
<220> FEATURE:
<223> OTHER INFORMATION: hstm1 Forward primer

<400> SEQUENCE: 8
tctggaagaa actgggctcc                                             20

<210> SEQ ID NO 9
<211> LENGTH: 20
<212> TYPE: DNA
<213> ORGANISM: Artificial Sequence
<220> FEATURE:
<223> OTHER INFORMATION: hstm1 Reverse primer

<400> SEQUENCE: 9
catgttgccc gtcttgtagg                                             20

<210> SEQ ID NO 10
<211> LENGTH: 20
<212> TYPE: DNA
<213> ORGANISM: Artificial Sequence
<220> FEATURE:
<223> OTHER INFORMATION: GAPDH Forward primer

<400> SEQUENCE: 10
ctacatggtc tacatgttcc                                             20

<210> SEQ ID NO 11
<211> LENGTH: 20
<212> TYPE: DNA
<213> ORGANISM: Artificial Sequence
<220> FEATURE:
<223> OTHER INFORMATION: GAPDH Reverse primer

<400> SEQUENCE: 11
ctgacaatct tgagtgagtt                                             20

<210> SEQ ID NO 12
<211> LENGTH: 20
<212> TYPE: DNA
<213> ORGANISM: Artificial Sequence
<220> FEATURE:
<223> OTHER INFORMATION: IGF-1 Forward primer

<400> SEQUENCE: 12
cctcttctac ctggcgctct                                             20

<210> SEQ ID NO 13
<211> LENGTH: 20
<212> TYPE: DNA
<213> ORGANISM: Artificial Sequence
```

```
<220> FEATURE:
<223> OTHER INFORMATION: IGF-1 Reverse primer

<400> SEQUENCE: 13
gggacttctg agtcttgggc                                                   20

<210> SEQ ID NO 14
<211> LENGTH: 21
<212> TYPE: DNA
<213> ORGANISM: Artificial Sequence
<220> FEATURE:
<223> OTHER INFORMATION: IGF-2 Forward primer

<400> SEQUENCE: 14
ggaccgcggc ttctacttca g                                                 21

<210> SEQ ID NO 15
<211> LENGTH: 21
<212> TYPE: DNA
<213> ORGANISM: Artificial Sequence
<220> FEATURE:
<223> OTHER INFORMATION: IGF-2 Reverse primer

<400> SEQUENCE: 15
gaccccggcg ggcacgcagg a                                                 21

<210> SEQ ID NO 16
<211> LENGTH: 21
<212> TYPE: DNA
<213> ORGANISM: Artificial Sequence
<220> FEATURE:
<223> OTHER INFORMATION: cyclin D1 Forward primer

<400> SEQUENCE: 16
gaacacttcc tctccaaaat g                                                 21

<210> SEQ ID NO 17
<211> LENGTH: 21
<212> TYPE: DNA
<213> ORGANISM: Artificial Sequence
<220> FEATURE:
<223> OTHER INFORMATION: cyclin D1 Reverse primer

<400> SEQUENCE: 17
gttctgctgg gcctggcgca g                                                 21

<210> SEQ ID NO 18
<211> LENGTH: 21
<212> TYPE: DNA
<213> ORGANISM: Artificial Sequence
<220> FEATURE:
<223> OTHER INFORMATION: hSTM1a Forward primer

<400> SEQUENCE: 18
tcatcaaagc ctacaagacg g                                                 21

<210> SEQ ID NO 19
<211> LENGTH: 21
<212> TYPE: DNA
<213> ORGANISM: Artificial Sequence
<220> FEATURE:
<223> OTHER INFORMATION: hSTM1a Reverse primer

<400> SEQUENCE: 19
ggtggacttc cggaggaagt t                                                 21
```

```
<210> SEQ ID NO 20
<211> LENGTH: 19
<212> TYPE: RNA
<213> ORGANISM: Artificial Sequence
<220> FEATURE:
<223> OTHER INFORMATION: scrambled-1 Forward siRNA

<400> SEQUENCE: 20
guccacauuc gacgcccac                                                        19

<210> SEQ ID NO 21
<211> LENGTH: 19
<212> TYPE: RNA
<213> ORGANISM: Artificial Sequence
<220> FEATURE:
<223> OTHER INFORMATION: scrambled-1 Reverse siRNA

<400> SEQUENCE: 21
gugggcgucg aauguggac                                                        19

<210> SEQ ID NO 22
<211> LENGTH: 19
<212> TYPE: RNA
<213> ORGANISM: Artificial Sequence
<220> FEATURE:
<223> OTHER INFORMATION: scrambled-2 Forward siRNA

<400> SEQUENCE: 22
agcgcugaca acaguuuca                                                        19

<210> SEQ ID NO 23
<211> LENGTH: 19
<212> TYPE: RNA
<213> ORGANISM: Artificial Sequence
<220> FEATURE:
<223> OTHER INFORMATION: scrambled-2 Reverse siRNA

<400> SEQUENCE: 23
ugaaacuguu gucagcgcu                                                        19

<210> SEQ ID NO 24
<211> LENGTH: 19
<212> TYPE: RNA
<213> ORGANISM: Artificial Sequence
<220> FEATURE:
<223> OTHER INFORMATION: G alpha i-1 Forward siRNA

<400> SEQUENCE: 24
gcacagagug acuacaucc                                                        19

<210> SEQ ID NO 25
<211> LENGTH: 19
<212> TYPE: RNA
<213> ORGANISM: Artificial Sequence
<220> FEATURE:
<223> OTHER INFORMATION: G alpha i-1 Reverse siRNA

<400> SEQUENCE: 25
ggauguaguc acucugugc                                                        19

<210> SEQ ID NO 26
<211> LENGTH: 19
<212> TYPE: RNA
<213> ORGANISM: Artificial Sequence
<220> FEATURE:
<223> OTHER INFORMATION: G alpha i-2 Forward siRNA
```

```
<400> SEQUENCE: 26
ggagugcuga agaaggagu                                                    19

<210> SEQ ID NO 27
<211> LENGTH: 19
<212> TYPE: RNA
<213> ORGANISM: Artificial Sequence
<220> FEATURE:
<223> OTHER INFORMATION: G alpha i-2 Reverse siRNA

<400> SEQUENCE: 27
acuccuucuu cagcacucc                                                    19

<210> SEQ ID NO 28
<211> LENGTH: 19
<212> TYPE: RNA
<213> ORGANISM: Artificial Sequence
<220> FEATURE:
<223> OTHER INFORMATION: G alpha i-3 Forward siRNA

<400> SEQUENCE: 28
agcugcuuac auucagugc                                                    19

<210> SEQ ID NO 29
<211> LENGTH: 19
<212> TYPE: RNA
<213> ORGANISM: Artificial Sequence
<220> FEATURE:
<223> OTHER INFORMATION: G alpha i-3 Reverse siRNA

<400> SEQUENCE: 29
gcacugaaug uaagcagcu                                                    19

<210> SEQ ID NO 30
<211> LENGTH: 21
<212> TYPE: DNA
<213> ORGANISM: Artificial Sequence
<220> FEATURE:
<223> OTHER INFORMATION: G alpha i-1 Forward primer

<400> SEQUENCE: 30
ggcggatgat gctcgccaac t                                                 21

<210> SEQ ID NO 31
<211> LENGTH: 21
<212> TYPE: DNA
<213> ORGANISM: Artificial Sequence
<220> FEATURE:
<223> OTHER INFORMATION: G alpha i-1 Reverse primer

<400> SEQUENCE: 31
gatgacgtct gttacagcat c                                                 21

<210> SEQ ID NO 32
<211> LENGTH: 21
<212> TYPE: DNA
<213> ORGANISM: Artificial Sequence
<220> FEATURE:
<223> OTHER INFORMATION: G alpha i-2 Forward primer

<400> SEQUENCE: 32
gtgactacat ccctacacag c                                                 21

<210> SEQ ID NO 33
```

```
<211> LENGTH: 21
<212> TYPE: DNA
<213> ORGANISM: Artificial Sequence
<220> FEATURE:
<223> OTHER INFORMATION: G alpha i-2 Reverse primer

<400> SEQUENCE: 33
gacggcatcg aacacaaact g                                              21

<210> SEQ ID NO 34
<211> LENGTH: 21
<212> TYPE: DNA
<213> ORGANISM: Artificial Sequence
<220> FEATURE:
<223> OTHER INFORMATION: G alpha i-3 Forward primer

<400> SEQUENCE: 34
gaaccgaatg catgaaagca t                                              21

<210> SEQ ID NO 35
<211> LENGTH: 21
<212> TYPE: DNA
<213> ORGANISM: Artificial Sequence
<220> FEATURE:
<223> OTHER INFORMATION: G alpha i-3 Reverse primer

<400> SEQUENCE: 35
tgatgacatc cgtaacagca t                                              21

<210> SEQ ID NO 36
<211> LENGTH: 19
<212> TYPE: RNA
<213> ORGANISM: Artificial Sequence
<220> FEATURE:
<223> OTHER INFORMATION: hstm1-1 Forward siRNA

<400> SEQUENCE: 36
ccgugcuguu guuccucau                                                 19

<210> SEQ ID NO 37
<211> LENGTH: 19
<212> TYPE: RNA
<213> ORGANISM: Artificial Sequence
<220> FEATURE:
<223> OTHER INFORMATION: hstm1-1 Reverse siRNA

<400> SEQUENCE: 37
augaggaaca acagcacgg                                                 19

<210> SEQ ID NO 38
<211> LENGTH: 19
<212> TYPE: RNA
<213> ORGANISM: Artificial Sequence
<220> FEATURE:
<223> OTHER INFORMATION: hstm1-2  Forward siRNA

<400> SEQUENCE: 38
uccagcgugu uguaccugc                                                 19

<210> SEQ ID NO 39
<211> LENGTH: 19
<212> TYPE: RNA
<213> ORGANISM: Artificial Sequence
<220> FEATURE:
<223> OTHER INFORMATION: hstm1-2 Reverse siRNA

<400> SEQUENCE: 39
```
gcagguacaa cacgcugga                                               19

<210> SEQ ID NO 40
<211> LENGTH: 19
<212> TYPE: RNA
<213> ORGANISM: Artificial Sequence
<220> FEATURE:
<223> OTHER INFORMATION: 1361/2279 Forward siRNA

<400> SEQUENCE: 40
ggggaucucc uacucucug                                               19

<210> SEQ ID NO 41
<211> LENGTH: 19
<212> TYPE: RNA
<213> ORGANISM: Artificial Sequence
<220> FEATURE:
<223> OTHER INFORMATION: 1361/2279 Reverse siRNA

<400> SEQUENCE: 41
cagagaguag gagauccccc                                              19

<210> SEQ ID NO 42
<211> LENGTH: 19
<212> TYPE: RNA
<213> ORGANISM: Artificial Sequence
<220> FEATURE:
<223> OTHER INFORMATION: 1509/2279 Forward siRNA

<400> SEQUENCE: 42
cugcugcucg acaccauca                                               19

<210> SEQ ID NO 43
<211> LENGTH: 19
<212> TYPE: RNA
<213> ORGANISM: Artificial Sequence
<220> FEATURE:
<223> OTHER INFORMATION: 1509/2279 Reverse siRNA

<400> SEQUENCE: 43
ugaugguguc gagcagcag                                               19

<210> SEQ ID NO 44
<211> LENGTH: 19
<212> TYPE: RNA
<213> ORGANISM: Artificial Sequence
<220> FEATURE:
<223> OTHER INFORMATION: 1322/2279 Forward siRNA

<400> SEQUENCE: 44
gccucagauc cgcaccaac                                               19

<210> SEQ ID NO 45
<211> LENGTH: 19
<212> TYPE: RNA
<213> ORGANISM: Artificial Sequence
<220> FEATURE:
<223> OTHER INFORMATION: 1322/2279 Reverse siRNA

<400> SEQUENCE: 45
guuggugcgg aucugaggc                                               19

<210> SEQ ID NO 46
<211> LENGTH: 19
<212> TYPE: RNA

```
<213> ORGANISM: Artificial Sequence
<220> FEATURE:
<223> OTHER INFORMATION: 1511/2279 Forward siRNA

<400> SEQUENCE: 46
gcugcucgac accaucauc                                                      19

<210> SEQ ID NO 47
<211> LENGTH: 19
<212> TYPE: RNA
<213> ORGANISM: Artificial Sequence
<220> FEATURE:
<223> OTHER INFORMATION: 1511/2279 Reverse siRNA

<400> SEQUENCE: 47
gcugcucgac accaucauc                                                      19

<210> SEQ ID NO 48
<211> LENGTH: 19
<212> TYPE: RNA
<213> ORGANISM: Artificial Sequence
<220> FEATURE:
<223> OTHER INFORMATION: 1015/2279 Forward siRNA

<400> SEQUENCE: 48
agaccuacac ggcugugua                                                      19

<210> SEQ ID NO 49
<211> LENGTH: 19
<212> TYPE: RNA
<213> ORGANISM: Artificial Sequence
<220> FEATURE:
<223> OTHER INFORMATION: 1015/2279 Reverse siRNA

<400> SEQUENCE: 49
uacacagccg uguaggucu                                                      19

<210> SEQ ID NO 50
<211> LENGTH: 19
<212> TYPE: RNA
<213> ORGANISM: Artificial Sequence
<220> FEATURE:
<223> OTHER INFORMATION: 1052/2279 Forward siRNA

<400> SEQUENCE: 50
ggugaugcug acgcuguac                                                      19

<210> SEQ ID NO 51
<211> LENGTH: 19
<212> TYPE: RNA
<213> ORGANISM: Artificial Sequence
<220> FEATURE:
<223> OTHER INFORMATION: 1052/2279 Reverse siRNA

<400> SEQUENCE: 51
guacagcguc agcaucacc                                                      19
```